US012727987B2

(12) United States Patent
El Azouzi et al.

(10) Patent No.: US 12,727,987 B2
(45) Date of Patent: Sep. 8, 2026

(54) FLOW RESTRICTING STENT-GRAFT

(71) Applicant: AORTO MEDICAL LLC, Tangier (MA)

(72) Inventors: Youssef El Azouzi, Tangier (MA); Saleem Abdul Ganiy, Santa Rosa, CA (US)

(73) Assignee: AORTO MEDICAL LLC., Tangier (MA)

( * ) Notice: Subject to any disclaimer, the term of this patent is extended or adjusted under 35 U.S.C. 154(b) by 1000 days.

(21) Appl. No.: 17/429,515

(22) PCT Filed: Feb. 14, 2020

(86) PCT No.: PCT/US2020/018323
§ 371 (c)(1),
(2) Date: Aug. 9, 2021

(87) PCT Pub. No.: WO2020/168216
PCT Pub. Date: Aug. 20, 2020

(65) Prior Publication Data

US 2022/0125571 A1 Apr. 28, 2022

Related U.S. Application Data

(60) Provisional application No. 62/902,462, filed on Sep. 19, 2019, provisional application No. 62/899,914, (Continued)

(51) Int. Cl.
*A61F 2/07* (2013.01)
*A61F 2/856* (2013.01)
(Continued)

(52) U.S. Cl.
CPC ................ *A61F 2/07* (2013.01); *A61F 2/856* (2013.01); *A61L 31/022* (2013.01); (Continued)

(58) Field of Classification Search
CPC .......... A61H 1/0244; A61H 2201/1659; A61H 2201/5028; A61H 2201/5061; (Continued)

(56) References Cited

U.S. PATENT DOCUMENTS 6,214,037 B1 4/2001 Mitchell et al.
8,672,993 B2 3/2014 Chuter et al.
(Continued)

FOREIGN PATENT DOCUMENTS

JP 2014525811 A 10/2014
WO 2011158045 A1 12/2011
(Continued)

OTHER PUBLICATIONS

Extended Search Report for related International Application No. 20755654.9; action dated Oct. 17, 2022; (8 pages).
(Continued)

*Primary Examiner* — Yashita Sharma
*Assistant Examiner* — Aren Patel
(74) *Attorney, Agent, or Firm* — K&L Gates LLP

(57) ABSTRACT

The presently described stent-graft includes a stent frame forming a cavity and frame wires extending around the stent frame perimeter. The stent frame is formed such that the cavity cross sectional area decreases along a first length of a flow restricting section to a cavity minimum cross sectional area and increases along a second length of the flow restricting section. The first length extends from a cavity proximal cross sectional area to the cavity minimum cross sectional area and the second length extends from the cavity minimum cross sectional area to a cavity distal cross sectional area. When placed within a patient's aorta, the stent-graft may help the treatment of congestive heart failure by increasing blood flow to the kidneys. The provided stent-
(Continued)

graft may also be adapted for placement within a patient's urethra to help the treatment of urinary incontinence.

37 Claims, 13 Drawing Sheets

Related U.S. Application Data filed on Sep. 13, 2019, provisional application No. 62/837,324, filed on Apr. 23, 2019, provisional application No. 62/816,395, filed on Mar. 11, 2019, provisional application No. 62/806,855, filed on Feb. 17, 2019.

(51) Int. Cl.
*A61L 31/02* (2006.01)
*A61F 2/04* (2013.01)
*A61F 2/848* (2013.01)

(52) U.S. Cl.
CPC ... *A61F 2002/047* (2013.01); *A61F 2002/072* (2013.01); *A61F 2002/8486* (2013.01); *A61F 2210/0014* (2013.01); *A61F 2250/0039* (2013.01)

(58) Field of Classification Search
CPC . A61H 2201/5097; B25J 9/0006; B25J 9/163; A61F 2/07; A61F 2/856; A61F 2002/047; A61F 2002/072; A61F 2002/8486; A61F 2210/0014; A61F 2250/0039; A61L 31/022
See application file for complete search history.

(56) References Cited

U.S. PATENT DOCUMENTS 8,870,938 B2 10/2014 Shalev et al.
9,597,204 B2 3/2017 Benary et al.
2008/0194905 A1* 8/2008 Walsh ................ A61M 60/869 600/17
2008/0228136 A1* 9/2008 Seward ............ A61M 25/1002 604/96.01
2010/0191167 A1 7/2010 Laufer
2011/0130819 A1 6/2011 Cragg et al.
2013/0172981 A1* 7/2013 Gross .................. A61B 5/0053 623/1.15
2014/0296963 A1* 10/2014 Akingba .................. A61F 2/07 623/1.13
2014/0350658 A1* 11/2014 Benary .................. A61F 2/856 623/1.35
2015/0073523 A1* 3/2015 Chobotov ................ A61F 2/07 623/1.13
2016/0310077 A1* 10/2016 Hunter .................. G16H 40/60
2017/0156846 A1* 6/2017 Wang ...................... A61F 2/915
2018/0147387 A1* 5/2018 Erbey, II ............ A61M 25/003
2018/0220589 A1 8/2018 Burden
2018/0353281 A1 12/2018 Nussinovitch

FOREIGN PATENT DOCUMENTS

WO 2017154025 A1 9/2017
WO 2017154025 A2 9/2017
WO 2018061002 A1 4/2018
WO 2018140637 A1 8/2018

OTHER PUBLICATIONS

Preliminary Report on Patentability for related International Application No. PCT/US2020/018323; action dated Aug. 26, 2021; (7 pages).
Examination Report for related Indian Application No. 202117041861; action dated Feb. 10, 2023; (5 pages).
International Search Report for related International Application No. PCT/US2020/018323; report dated Aug. 20, 2020; (2 pages).
Positive Written Opinion for related International Application No. PCT/US2020/018323; report dated Aug. 20, 2020; (5 pages).
Japanese Office Action for related Japanese Application No. 2021-546829; action dated Feb. 28, 2022; (9 pages).
Preliminary Report for related Brazilian Application No. BR112021016124-4; action dated Jul. 22, 2025; (4 pages).

* cited by examiner

FLOW RESTRICTING STENT-GRAFT

PRIORITY CLAIM

The present application is a National Phase of International Application No. PCT/US2020/018323, filed Feb. 14, 2020, which claims priority to Provisional Application No. 62/806,855, filed Feb. 17, 2019, Provisional Application No. 62/816,395, filed Mar. 11, 2019, Provisional Application No. 62/837,324, filed Apr. 23, 2019, Provisional Application No. 62/899,914, filed Sep. 13, 2019, and Provisional Application No. 62/902,462, filed Sep. 19, 2019. The entire contents of each are incorporated herein by reference and relied upon.

BACKGROUND

A significant portion of the population is diagnosed annually with congestive heart failure. Congestive heart failure (CHF) is a chronic progressive condition that affects the pumping power of a patient's heart muscles. It develops when a patient's heart cannot pump enough blood volume to the patient's body, eventually causing blood and other fluids to back up inside the patient's lungs, abdomen, liver, and/or lower body. Congestive heart failure specifically refers to the stage in which fluid builds up around the heart and causes it to pump inefficiently. Congestive heart failure can progress through various stages, of which the early stages can be managed by lifestyle changes and medications. Left untreated, however, congestive heart failure can progress to be life-threatening and thus various treatment methods may be prescribed to a patient for managing congestive heart failure.

One way to help treat CHF is with renin-angiotensin-aldosterone-system (RAAS) antagonist medication, which improves the survival of patients with chronic CHF. However, CHF's progression and associated decline in cardiac output causes a decreased glomerular filtration rate (GFR), a calculation that determines how well blood is filtered by the kidneys, due to falling intra-aortic pressure and aortic branch hypoperfusion in the heart. Once the GFR reaches a threshold level due to the decreased kidney function, a significant amount of aldosterone and/or Angiotensin II residues may remain in a patient's blood circulation despite maximal pharmaceutical ACE-inhibitor and ARB activity. Pharmaceutically-driven renin inhibitors have been shown to cause markedly limited improvement in CHF patients compared with placebos and have been shown to cause significantly more adverse effects in CHF patients including hyperkalemia, hypotension and renal failure when compared to ACE-inhibitor use.

Another way to help manage CHF, particularly end-stage CHF, is with conventional intra-aortic balloon pumps as well as other percutaneous ventricular unloading devices (e.g., TandemHeart® and Impella®). Such conventional percutaneous ventricular unloading devices are minimally-invasive and helpful in stabilizing patients presenting cardiogenic shock; however, they are only designed for short-term usage. For instance, such devices are dependent on external console triggers for intervention via a femoral catheter. Therefore, conventional percutaneous ventricular unloading devices may be helpful for the treatment of acute cardiac decompensation, but are ineffective for chronic, long-term CHF management.

Another way to help manage CHF is with a non-invasive pump device that may be deployed at a heart's descending aorta level to provide long-term circulatory support by assisting the heart in pumping blood. Such a pump device does not require open surgery, but does require a battery that is connected through a patient's skin and needs consistent recharging. Therefore, such a device may be cumbersome for a patient to have to consistently recharge the battery, which also requires the patient be in an area that provides access to electrical power for charging the battery. Having such consistent access to electrical power is not available for all patients. In addition, patients who have significant cognitive disabilities, such as due to stroke, Alzheimer's or dementia, are unable to be treated long-term with these devices because of the patients' inability to properly control and maintain the device. Such patients are therefore left with limited treatment options.

Additionally, a significant portion of the population may experience urinary incontinence. Urinary incontinence is the involuntary leakage of urine, meaning a person urinates when they do not want to, and may be the result of a patient's urinary sphincter control being either lost or weakened. An example of urinary incontinence is stress incontinence, which is an involuntary leakage of urine due to increased pressure, such as a person coughing or sneezing. One method of treating urinary stress incontinence is a sling surgical procedure, which involves a surgeon creating a "sling" implant out of xenograft mesh or human tissue. The surgeon positions the "sling" implant under a patient's urethra to lift and support the urethra and the neck of the patient's bladder to help prevent urine leakage. The sling procedure, however, is a considerably lengthy procedure. The "sling" implant is also not easily removable should a situation arise in which the "sling" implant is no longer needed or it is otherwise desired for it to be removed. A patient must undergo open invasive surgery to remove the xenograft mesh, and may require hospitalization post-surgery and/or additional surgical procedures. Additionally, there has been a high incidence rate of patient complications from the mesh "sling" implants. For instance, the xenograft mesh may erode and fuse with a patient's nerves in the pelvic area, which can result in chronic, debilitating pain.

BRIEF SUMMARY OF THE INVENTION

The present disclosure provides a new and innovative stent-graft. The stent-graft may be tapered in order to help create a controlled, proximal perfusion gradient of aortic blood to achieve more complete renal artery filling and direct a larger volume of blood to the kidneys. The stent-graft may also be tapered in order to help prevent urinary incontinence. In light of the disclosures herein, and without limiting the scope of the invention in any way, in a first aspect of the present disclosure, which may be combined with any other aspect listed herein unless specified otherwise, a stent includes a stent frame forming a cavity and a plurality of frame wires extending around a perimeter of the stent frame. The cavity extends from a proximal opening of the stent to a distal opening of the stent, and the stent frame is adapted for a fluid to flow through the cavity from the proximal opening to the distal opening. The stent frame is formed such that the cavity cross sectional area decreases along a first length of a flow restricting section to a crescent-shaped cavity minimum cross sectional area and increases along a second length of the flow restricting section. The first length extends from a cavity proximal cross sectional area to the crescent-shaped cavity minimum cross sectional area and the second length extends from the crescent-shaped cavity minimum cross sectional area to a cavity distal cross sectional area.

In a second aspect of the present disclosure, which may be combined with any other aspect listed herein unless specified otherwise, the perimeter of the stent frame along the flow restricting section includes a concave surface extending into the cavity.

In a third aspect of the present disclosure, which may be combined with any other aspect listed herein unless specified otherwise, one or more of the plurality of frame wires includes a curved portion extending along the concave surface.

In a fourth aspect of the present disclosure, which may be combined with any other aspect listed herein unless specified otherwise, the concave surface of the stent frame perimeter includes a first piece of fabric and the remaining perimeter includes a second piece of fabric, wherein the first piece is connected to the second piece.

In a fifth aspect of the present disclosure, which may be combined with any other aspect listed herein unless specified otherwise, the stent-graft is configured such that the stent frame and the plurality of frame wires expand and contract to increase and decrease the cross sectional area of the cavity.

In a sixth aspect of the present disclosure, which may be combined with any other aspect listed herein unless specified otherwise, the stent frame is configured such that the minimum cross sectional area of the cavity is equal to between 2% to 40% of the proximal cross sectional area of the cavity.

In a seventh aspect of the present disclosure, which may be combined with any other aspect listed herein unless specified otherwise, the stent frame is configured such that the minimum cross sectional area of the cavity includes a left flow end, a central flow portion, and a right flow end, and the left flow end and the right flow end each respectively having a width greater than the central flow portion.

In an eighth aspect of the present disclosure, which may be combined with any other aspect listed herein unless specified otherwise, the stent frame includes an outer wall and an inner wall and the outer wall is connected to the inner wall along a line such that fluid flowing from the proximal opening through the cavity is directed to the left flow end and the right flow end and prevented from reaching the central flow portion.

In a ninth aspect of the present disclosure, which may be combined with any other aspect listed herein unless specified otherwise, the stent frame is configured such that the minimum cross sectional area of the cavity includes a left flow end, a central flow portion, and a right flow end, and the left flow end and the right flow end each respectively having a width less than the central flow portion.

In a tenth aspect of the present disclosure, which may be combined with any other aspect listed herein unless specified otherwise, the stent frame at the minimum cross sectional area of the cavity includes an outer wall and an inner wall, and the stent frame is configured such that the inner wall of the central flow portion curves away from the outer wall of the central flow portion.

In an eleventh aspect of the present disclosure, which may be combined with any other aspect listed herein unless specified otherwise, the stent frame at the minimum cross sectional area of the cavity includes an outer wall and an inner wall, and a first bridge connects the outer wall to the inner wall where the left flow end meets the central flow portion, and a second bridge connects the outer wall to the inner wall where the right flow end meets the central flow portion.

In a twelfth aspect of the present disclosure, which may be combined with any other aspect listed herein unless specified otherwise, the stent frame at the minimum cross sectional area of the cavity includes an outer wall and an inner wall, and the outer wall and the inner wall at the left flow end, and the outer wall and the inner wall at the right flow end, are respectively sutured together such that fluid is prevented from flowing through the left flow end and the right flow end.

In a thirteenth aspect of the present disclosure, which may be combined with any other aspect listed herein unless specified otherwise, the stent frame includes an outer wall and an inner wall and the outer wall is connected to the inner wall along a line such that fluid flowing from the proximal opening through the cavity is directed to the central flow portion and prevented from reaching the left flow end and the right flow end.

In a fourteenth aspect of the present disclosure, which may be combined with any other aspect listed herein unless specified otherwise, each respective frame wire of the plurality of frame wires includes an undulating portion.

In a fifteenth aspect of the present disclosure, which may be combined with any other aspect listed herein unless specified otherwise, the plurality of frame wires includes a plurality of flow-restricting frame wires within the flow restricting section of the stent frame.

In a sixteenth aspect of the present disclosure, which may be combined with any other aspect listed herein unless specified otherwise, each respective flow-restricting frame wire includes an undulating portion and a curved portion.

In a seventeenth aspect of the present disclosure, which may be combined with any other aspect listed herein unless specified otherwise, a radius of curvature between the undulating portion and the curved portion of each respective flow-restricting frame wire is between 0.1 to 1.0 millimeters.

In an eighteenth aspect of the present disclosure, which may be combined with any other aspect listed herein unless specified otherwise, at least one of the plurality of flow-restricting frame wires is configured to contact, when disposed within an abdominal aorta, at least 40% of the perimeter of the abdominal aorta, at least some of the time.

In a nineteenth aspect of the present disclosure, which may be combined with any other aspect listed herein unless specified otherwise, the plurality of flow-restricting frame wires have equal perimeter lengths.

In a twentieth aspect of the present disclosure, which may be combined with any other aspect listed herein unless specified otherwise, each respective flow-restricting frame wire of the plurality of frame wires is configured from a shape-memory material.

In a twenty-first aspect of the present disclosure, which may be combined with any other aspect listed herein unless specified otherwise, the shape-memory material is nitinol.

In a twenty-second aspect of the present disclosure, which may be combined with any other aspect listed herein unless specified otherwise, the plurality of flow-restricting frame wires includes a first flow-restricting frame wire extending around the perimeter of the stent frame at the minimum cross sectional area of the cavity and a second flow-restricting frame wire disposed around the first flow-restricting frame wire, and the second flow-restricting frame wire has a shape memory transition temperature greater than the first flow-restricting frame wire.

In a twenty-third aspect of the present disclosure, which may be combined with any other aspect listed herein unless specified otherwise, each respective flow-restricting frame wire includes a second flow-restricting frame wire disposed around a first flow-restricting frame wire, and wherein the second flow-restricting frame wire has a shape memory transition temperature greater than the first flow-restricting frame wire.

In a twenty-fourth aspect of the present disclosure, which may be combined with any other aspect listed herein unless specified otherwise, the plurality of frame wires includes a fixation frame wire at the proximal opening of the stent, the fixation frame wire configured to fix the stent to an artery wall.

In a twenty-fifth aspect of the present disclosure, which may be combined with any other aspect listed herein unless specified otherwise, the stent frame is constructed of one or more fabrics selected from the group consisting of polyurethane, polyester, and polytetrafluoroethylene.

In a twenty-sixth aspect of the present disclosure, which may be combined with any other aspect listed herein unless specified otherwise, the stent further includes a wireless percutaneous pressure monitor near at least one of the proximal or distal opening.

In a twenty-seventh aspect of the present disclosure, which may be combined with any other aspect listed herein unless specified otherwise, the wireless percutaneous pressure monitor is integrated with the stent-graft based on at least one of suturing, magnets, or a mechanical clip.

In a twenty-eighth aspect of the present disclosure, which may be combined with any other aspect listed herein unless specified otherwise, the stent further includes two kidney graft branches in fluid communication with the cavity.

In a twenty-ninth aspect of the present disclosure, which may be combined with any other aspect listed herein unless specified otherwise, the stent further includes at least one secondary graft branch in fluid communication with the cavity, and the at least one secondary graft branch includes a fluid volume reducing portion that reduces the cross-sectional area of the at least one secondary graft branch.

In a thirtieth aspect of the present disclosure, which may be combined with any other aspect listed herein unless specified otherwise, the stent is configured such that each respective kidney graft branch of the two kidney graft branches may be inserted within a respective renal artery while the at least one secondary graft branch is inserted within a superior mesenteric artery or a coeliac trunk artery.

In a thirty-first aspect of the present disclosure, which may be combined with any other aspect listed herein unless specified otherwise, the stent is configured such that the proximal opening resides in the thoracic aorta while each respective kidney graft branch of the two kidney graft branches is inserted within a respective renal artery. The stent additionally includes a blocking sleeve configured to block fluid flow from the intercostal artery branches when the stent is disposed within an aorta of a patient.

In a thirty-second aspect of the present disclosure, which may be combined with any other aspect listed herein unless specified otherwise, the stent frame is formed with more than one flow restricting section.

In a thirty-third aspect of the present disclosure, which may be combined with any other aspect listed herein unless specified otherwise, a stent graft includes a stent frame forming a cavity, a fixation frame wire, a seal frame wire, and a flow-restricting frame wire. The cavity extends from a proximal opening of the stent to a distal opening of the stent. The stent frame is adapted for a fluid to flow through the cavity from the proximal opening to the distal opening. The fixation frame wire extends around a perimeter of the stent frame at the proximal opening. The seal frame wire extends around the perimeter of the stent frame. The flow-restricting frame wire extends around the perimeter of the stent frame at the distal opening. The stent frame is formed such that a cross sectional area of the cavity decreases from the proximal opening to a crescent-shaped minimum cross sectional area of the cavity at the distal opening.

In a thirty-fourth aspect of the present disclosure, which may be combined with any other aspect listed herein unless specified otherwise, the flow-restricting frame wire prevents fluid below a threshold fluid pressure from flowing through the distal opening.

In a thirty-fifth aspect of the present disclosure, which may be combined with any other aspect listed herein unless specified otherwise, the stent frame is formed such that the crescent-shaped minimum cross sectional area includes curled portions.

In a thirty-sixth aspect of the present disclosure, which may be combined with any other aspect listed herein unless specified otherwise, the stent frame has a length such that when placed within a patient's urethra, the proximal opening and the distal opening are between a bladder neck sphincter and a secondary sphincter.

In a thirty-seventh aspect of the present disclosure, which may be combined with any other aspect listed herein unless specified otherwise, the stent frame has a length such that when placed within a patient's urethra, the fixation frame wire and the seal frame wire are between a bladder neck sphincter and a secondary sphincter, and the flow-restricting frame wire is between the secondary sphincter and a urethral opening.

DETAILED DESCRIPTION

Figure 1B:
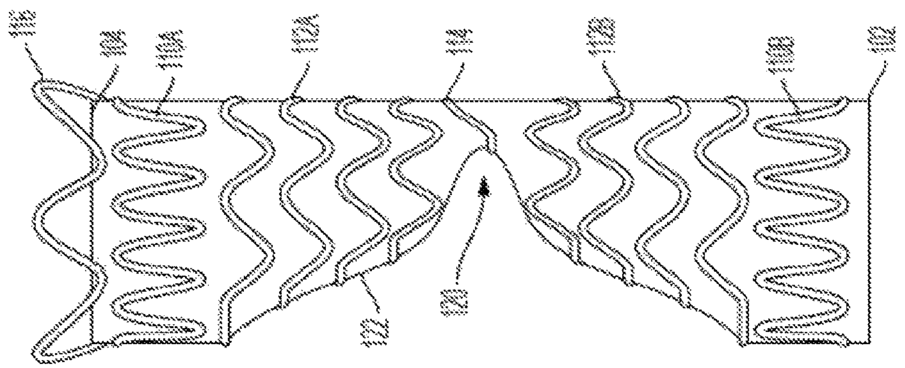
FIGS. 1A and 1B show an isometric and side view, respectively, of an example stent-graft, according to an aspect of the present disclosure.

The present disclosure, in part, provides a long-term, minimally-invasive treatment to help lengthen the survival time of a patient with end-stage CHF. In particular, the present disclosure provides a mechanical, interventional approach to upstream renin inhibition as a patient's resistance develops towards downstream RAAS antagonist medication in end-stage CHF patients. More specifically, the present disclosure provides a tapered flow modulator stent that may be placed in a patient's abdominal aorta to modulate systemic perfusion levels in order to improve a CHF patient's blood distribution efficiency and help prevent further systemic fluid retention triggered by RAAS hyperactivity. As low cardiac output in CHF patients contributes to excessive RAAS stimulation and thus systemic edema and hypervolemia, the provided stent-graft's infrarenal segment is tapered in order to help create a controlled, proximal perfusion gradient of aortic blood to achieve more complete renal artery filling and ultimately direct a larger volume of blood to the kidneys. Thus, the tapered configuration to create the perfusion gradient may bring about inhibition of the RAAS as well as systemic decongestion via mechanically increased diuresis.

A major step in the pathophysiology of heart failure is hypoperfusion of a patient's renal organs due to their subsequent secretion of harmful hormones that cause remodeling of the patient's heart muscle and ultimately causes reduction in its efficiency and thus further reduction in volume output. When placed in a patient's abdominal aorta, the presently disclosed stent-graft helps redistribute blood in the patient's body such that blood flow bound for the patient's lower extremities is diverted to the patient's kidneys in order to inhibit the secretion of the harmful hormones. Diverting blood flow to the patient's kidneys also helps enhance patient diuresis and reduce symptoms of volume overload typically observed in heart failure patients.

Additionally, the provided stent has an overall structure that may enhance the stent's fixation to a patient's aortic wall or other cavity to counteract long-term displacement forces more effectively than conventional stent-grafts. Conventional endovascular stent-grafts typically treat aneurysms, and the middle portion of such grafts typically exert little to no radial force on a patient's aortic wall because the luminal diameter of the aorta widens at the level of the aneurysm. Thus, only the proximal and distal ends of conventional stent-grafts typically prevent dislodgment of the stent via radial force. Conversely, the configuration of the presently disclosed stent-graft with a consistent outer diameter enables a greater portion of the stent-graft body to be in contact with the aortic wall circumference, and thus allows a greater portion of the stent-graft body to contribute to preventing migration of the stent and endoleak occurrence. In addition, the presently disclosed stent-graft has a substantially consistent perimeter, enabling a greater ease of manufacturing as compared to other typical tapered stents used in different treatment applications. The provided stent-graft is also a passive device that does not require a battery or any other power source.

In some example implementations, to help maximize the benefit to the renal organs, the provided stent may be used in combination with two balloon-expandable peripheral stents that are deployed at the proximal segments of both renal arteries. Such example implementations may increase the renal arteries' respective baseline diameters for enhanced blood flow accommodation. Accordingly, in view of the above advantages, by implementing the provided stent with conventional clinical regimen protocol, the provided stent may complement current standards of care for more effective hemodynamic stabilization in CHF patients over the short and long term.

The present disclosure also provides a treatment to help prevent urinary incontinence. Some embodiments of the provided stent-graft are adapted to be inserted within a patient's urethra. Such embodiments of the stent-graft prevent fluid from passing through the stent-graft until the fluid pressure upstream the stent-graft meets a threshold. The stent-graft may therefore replace the function of a patient's urethral sphincter that may have weakened or that the patient has lost control of, leading to the patient's urinary incontinence. For instance, when a patient does not have to urinate, the stent-graft is closed and prevents urine from passing through. As a patient's bladder fills with urine and the patient needs to urinate, however, the urine's hydrostatic pressure increases causing the stent-graft to open and allow urine to pass through. In this way, the provided stent-graft may help prevent urinary incontinence.

The surgical procedure to insert the provided stent-graft into a patient's urethra is significantly shorter in duration than the sling surgical procedure. The provided stent-graft is also more easily removable if it is no longer needed or otherwise needs to be explanted. Additionally, the provided stent-graft may be constructed of a fabric with metal frame wires, or other suitable, medical-grade materials, thus eliminating the complications that may arise with mesh implants.

Figure 1A:

FIGS. 1A and 1B show a perspective and side view, respectively, of an example stent-graft, according to an aspect of the present disclosure. The example stent-graft 100 includes a stent frame 130 that forms a cavity 132 extending from an opening at a proximal end 104 of the stent-graft 100 to an opening at a distal end 102 of the stent-graft 100. Thus, a fluid (e.g., blood) may flow into the proximal opening, through the cavity, and out the distal opening. The stent frame 130 may be formed from a single piece of fabric or other suitable, medical-grade material. The stent-frame 130 may alternatively be formed from more than one piece of fabric or other suitable, medical-grade material that are connected to one another. For instance, in some examples, the stent frame 130 may be formed from one of polyurethane, polyester, or polytetrafluoroethylene, or a combination thereof. In some examples, the stent frame 130 material may have a thickness between 0.05 and 0.90 mm. The example stent-graft 100 may have a length from the proximal end 104 to the distal end 102 in a range of 15-100 mm, in various examples.

The example stent-graft 100 may also include one or more seal frame wires 110A, 110B extending around the perimeter of the stent frame 130. The one or more seal frame wires 110A, 110B may extend around the stent frame 130 at its largest perimeter, for instance, outside of the flow restricting section 118 described below. The example stent-graft 100 may include one or more fixation frame wires 116, which will be described in more detail below. For instance, the stent-graft 100 may include a fixation frame wire 116 at one or both of the proximal end 104 and the distal end 102 of the stent-graft 100. The example stent-graft 100 may also include a plurality of flow-restricting frame wires 112A, 112B, 114 extending around the perimeter of the stent frame 130 within the flow restricting section 118. The flow-restricting frame wires 112A, 112B, 114 will be described in more detail below as well. It should be appreciated that only some of the frame wires within the flow restricting section 118 have been indicated with reference numerals on the illustrated figures for the sake of clarity.

The example stent frame 130 is formed to include a flow restricting section 118 or lobular obstruction. Within the flow restricting section 118, the cross sectional area of the cavity 132 decreases from a proximal cross sectional area (e.g., having a diameter between 20-42 mm) equal to the cross sectional area at the proximal end 104 opening to a minimum cross sectional area 120, and increases from the minimum cross sectional area 120 to a distal cross sectional area equal to the cross sectional area at the distal end 102 opening. The cross sectional area of the cavity 132 may decrease upstream the minimum cross sectional area 120 such that, in some examples, half way between the proximal end 104 and the minimum cross sectional area 120 the cross sectional area of the cavity is between 40-90% (e.g., 80%) of the cross sectional area at the proximal end 104. In other examples, such half-way cavity cross sectional area may be between 40-75% (e.g., 60%).

The minimum cross sectional area 120 may be equal to between 2-40% (e.g., 20%) of the cross sectional area at the proximal end 104, in some aspects. In such aspects, the stent-graft 100 obstructs blood from flowing through between 60-98% (e.g., 80%) of the cross sectional area of the patient's abdominal aorta at the minimum cross sectional area 120 of the stent-graft 100. In other aspects, the minimum cross sectional area 120 may be equal to between 5-20% (e.g., 6%) of the cross sectional area at the proximal end 104.

The cross sectional area of the cavity 132 may increase downstream the minimum cross sectional area 120 such that, in some examples, half way between the minimum cross sectional area 120 and the distal end 102 the cross sectional area of the cavity is between 40-90% (e.g., 80%) of the cross sectional area at the distal end 102. In other examples, such half-way cavity cross sectional area may be between 40-75% (e.g., 50%). The cross sectional area of the cavity 132 half way between the proximal end 104 and the minimum cross sectional area 120 may, in various instances, be equal to the cross sectional area of the cavity 132 half way between the minimum cross sectional area 120 and the distal end 102. The cross sectional area of the cavity 132 may decrease and increase symmetrically along the length of the stent-graft 100. In some aspects, the cross sectional area of the proximal end 104 opening may be equal to the cross sectional area of the distal end 102 opening.

The decrease in cross sectional area of the cavity 132 causes the fluid pressure of a fluid flowing through the cavity 132 to increase upstream the minimum cross sectional area 120 as less fluid is able to pass through the decreasingly smaller cavity opening. The increased fluid pressure upstream the minimum cross sectional area 120 may help increase the amount of blood directed to the renal arteries when the example stent-graft 100 is inserted within a patient's abdominal aorta. The increase in the cross sectional area of the cavity 132 downstream the minimum cross sectional area 120 helps the example stent-graft 100 remain fixed to a patient's aorta walls.

In some aspects of the present disclosure, the example stent frame 130 may be formed to include more than one flow restricting section 118 or lobular obstruction. For instance, the stent frame 130 may be formed with two flow restricting sections 118 such that the cross sectional area of the cavity 132 decreases from a first cross sectional area (e.g., the proximal end 104 cross sectional area) to a second cross sectional area (e.g., a first minimum cross sectional area), increases to a third cross sectional area, decreases to a fourth cross sectional area (e.g., a second minimum cross sectional area), and increases to a fifth cross sectional area (e.g., the distal end 102 cross sectional area). The third cross sectional area may be equal to or less than the first cross sectional area. In some examples, the second cross sectional area may be equal to the fourth cross sectional area. A stent frame 130 formed with more than one flow restricting section 118 may help reduce the turbulent flow of blood through the stent-graft 100. More than one flow restricting section 118 may also help reduce the degradation of red blood cells.

As a patient's heart cyclically pumps blood through systolic and diastolic phases, the blood pressure cycles in the patient's aorta. In various aspects, the example stent-graft 100 is formed such that the cavity 132 is expandable at the minimum cross sectional area 120. For instance, the stent frame 130 may be formed from a material capable of flexing in response to changes in fluid pressure (e.g., polyurethane and polyester). The frame wires 110A, 110B, 112A, 112B, 114 may be formed from a material capable of flexing and retaining its shape, such as a shape-memory material (e.g., nitinol). In various examples, the example stent-graft 100 may be formed such that, when placed within a patient's aorta, the minimum cross sectional area 120 (e.g., 45 $mm^2$) is equal to between 2-30% (e.g., 20%) of the cross sectional area of the proximal opening (e.g., 225 $mm^2$) during systole. During diastole, however, the minimum cross sectional area 120 (e.g., 67.5 $mm^2$) is equal to between 4-40% (e.g., 30%) of the cross sectional area of the proximal opening. In various examples, the stent-graft 100 may be formed such that, when placed within a patient's aorta, the blood pressure inside the stent-graft 100 upstream the minimum cross sectional area 120 is between 90-150 mmHg during systole and between 50-100 mmHg during diastole.

In various aspects of the present disclosure, the stent frame 130 of the example stent-graft 100 is formed with a concave surface 106 gradually extending into the cavity 132 along the flow restricting portion 118 to decrease the cross sectional area of the cavity 132. As illustrated in FIGS. 1A and 1B, in some examples, the stent frame 130 may be formed with an indentation 134 so that fluid flowing through the cavity 132 is funneled to the minimum cross sectional area 120 of the cavity 132. However, in other examples (e.g., FIGS. 3A and 3B), the stent frame 130 may be formed without such an indentation 134.

As a patient moves around, such as engaging in physical activity, the patient's blood accordingly moves around within the patient's body as well. Thus, when a stent is placed within a patient's aorta, the displacement forces that the patient's blood applies on the stent can vary based on the patient's movements. In various aspects, to help limit undesired axial movement of the stent within the patient, the example stent-graft 100 is configured such that the stent frame 130, and the frame wires (e.g., 112A, 112B), within the flow restricting portion 118 have crescent shapes. The crescent configuration allows for a gradually tapered stent-graft 100 decreasing from the proximal end 104 to the minimum cross sectional area 120 and increasing to the distal end 102. The crescent configuration also helps maintain contact between the outer surface of the stent-graft 100 and the aortic wall to assist in fixing the stent-graft 100 in place. For example, the crescent configuration may enable at least portions of the stent-graft 100 within the flow restricting portion 118 to contact equal to or greater than 50% of the aortic wall's circumference. In such examples, the stent-graft 100 may exert opposing forces on opposite ends of the aortic wall. The opposing forces may help fix the stent-graft 100 in place and prevent undesired axial movement.

Figure 2:
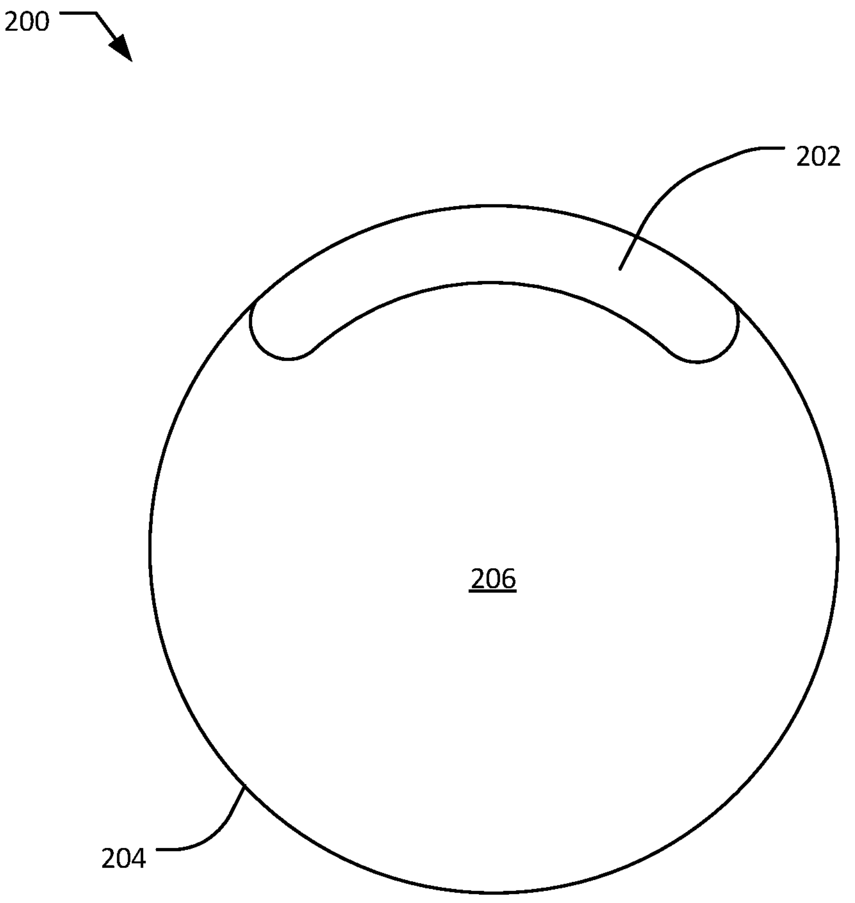
FIG. 2 shows a cross section at the minimum cross sectional area of the example stent-graft of FIGS. 1A and 1B within an aortic vessel, according to an aspect of the present disclosure.

FIG. 2 shows a cross section 200 at the minimum cross sectional area 202 of the example stent-graft 100 within an aortic vessel 204, according to an aspect of the present disclosure. The minimum cross sectional area 202 has a crescent shape, for example, maintained by the crescent-shaped frame wire 114. Because the crescent shape of the minimum cross sectional area 202 does not contact equal to or greater than 50% of the wall of the aortic vessel 204, it does not place opposing forces on opposite sides of the wall of the aortic vessel. The example stent-graft 100 instead relies upon the stent frame 130, and frame wires (e.g., 112A, 112B) upstream and downstream the minimum cross sectional area 120, which do contact equal to or greater than 50% of the wall of the aortic vessel 204, to help fix the stent-graft 100 and prevent undesired axial movement. Also shown is an area 206 of the aortic vessel 204 in which blood is obstructed from flowing. Instead, the blood flows through the minimum cross sectional area 202 of the cavity of the example stent-graft 100.

Figure 3B:
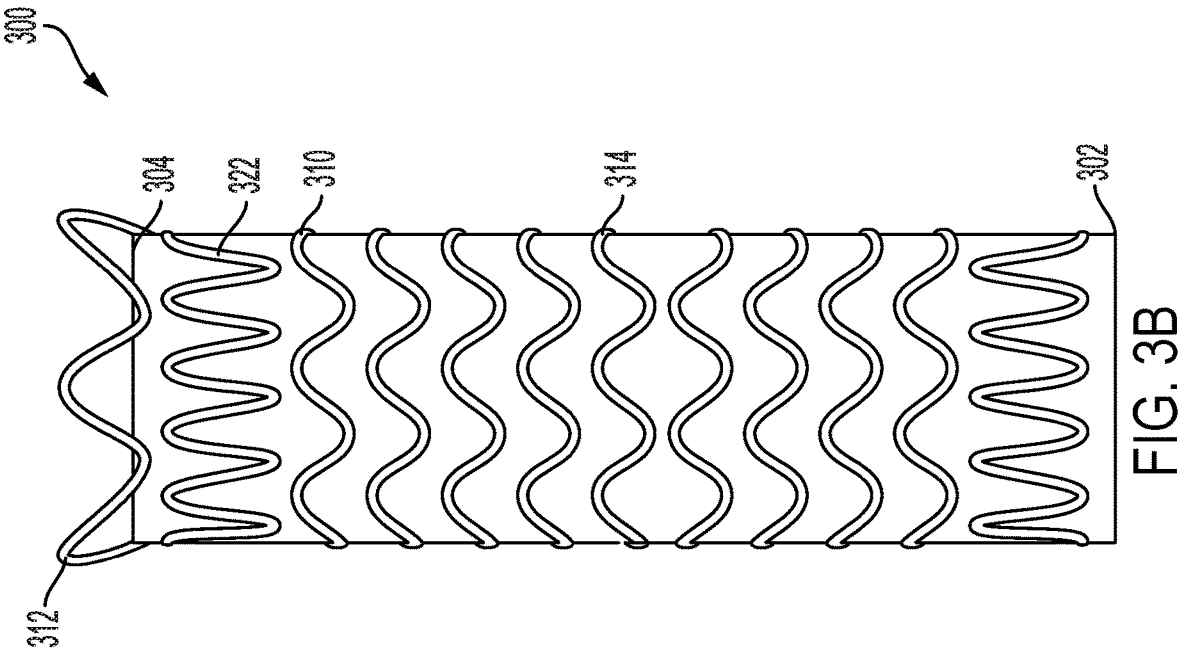
FIGS. 3A and 3B show an isometric and side view, respectively, of an example stent-graft with a minimum cross sectional area that includes flow ends, according to an aspect of the present disclosure.
Figure 3A:
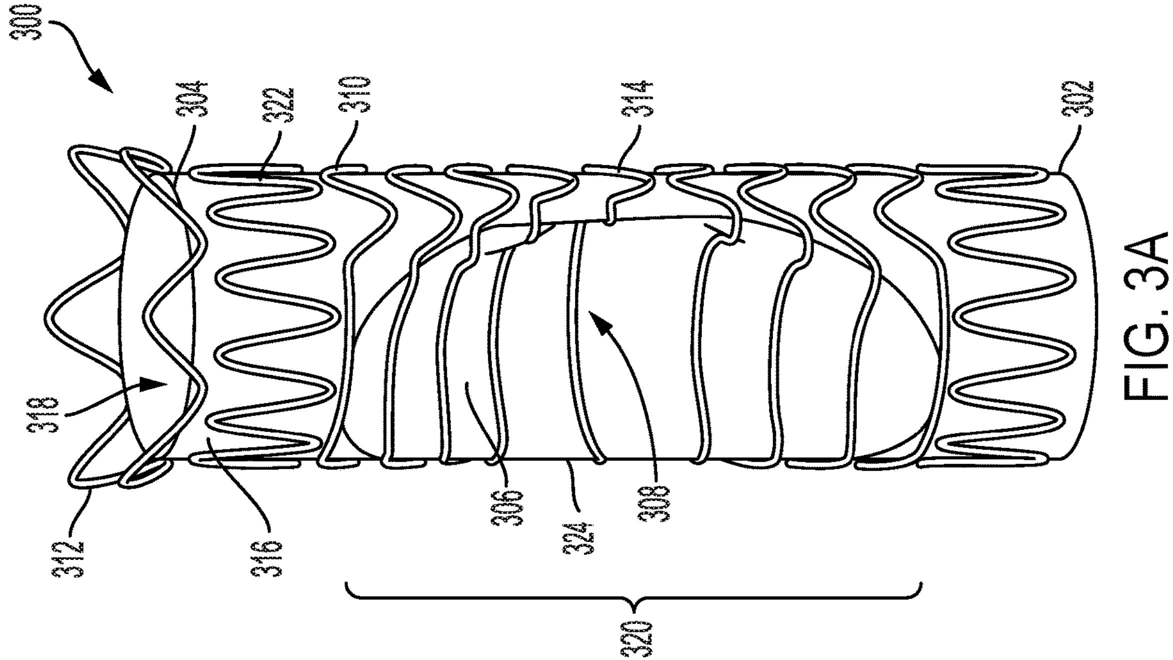

FIGS. 3A and 3B show a perspective and side view, respectively, of an example stent-graft with a minimum cross sectional area that includes flow ends, according to an aspect of the present disclosure. The example stent-graft 300 includes a stent frame 316 that forms a cavity 318 extending from an opening at a proximal end 304 of the stent-graft 300 to an opening at a distal end 302 of the stent-graft 300. The example stent frame 316 may also include a concave surface 306 extending within the cavity 318 to form a flow restricting portion 320. The flow restricting portion 320 reduces the cross sectional area of the cavity 318 to a minimum cross sectional area 308. The example stent-graft 300 may also include a plurality of frame wires 310, 314, a seal frame wire 322, and a fixation frame wire 312, which will be described in more detail below.

As is shown in FIGS. 3A and 3B, the example stent frame 316 is formed such that the minimum cross sectional area 308 of the cavity 318 extends half of the outer perimeter of the proximal end 304 of the stent frame 316. For instance, the side view shown in FIG. 3B illustrates that the stent frame 316 is formed such that one is prevented from viewing the concave surface 306 when viewing the example stent-graft 300 from the side. Stated differently, the example stent frame 316 is formed without the indentations 134 that the example stent frame 130 is formed with, and instead has flow ends 324. In other examples, the stent-graft 300 may be formed such that the minimum cross sectional area 308 of the cavity extends more than half of the outer perimeter of the proximal end 304 of the stent frame 316. The configuration of the example stent frame 316 to include the flow ends 324, instead of the indentation, enables the stent frame 316 at the minimum cross sectional area 308 to place outward fixation force on at least 50% of the aorta circumference. The added fixation force, as compared to the example stent-graft 100 with indentations 134, further helps limit movement of the example stent-graft 300 when placed within a patient's aorta.

Additionally, the frame wires 310 surrounding the stent-graft 300 within the flow restricting portion 320 may have a radius of curvature between the portion of the frame wire 310 that contacts the outer perimeter of the stent-graft 300 and the portion that contacts the concave surface 306. Stated differently, each of the frame wires 310 within the flow restricting portion 320 bend around the flow end 324 with a radius of curvature. In various instances, such radius of curvature of the frame wires 310 within the flow restricting portion 320 may be between 0.1 to 1.0 millimeters.

The consistent outer perimeter of the stent frame 316 that the flow ends 324 provide increases manufacturing efficiency. For instance, the indentations of the example stent-graft 100 may require more complicated folding patterns for manufacturing. By eliminating the indentations, the example stent-graft 300 may be manufactured with increased ease and speed.

Figure 4A:
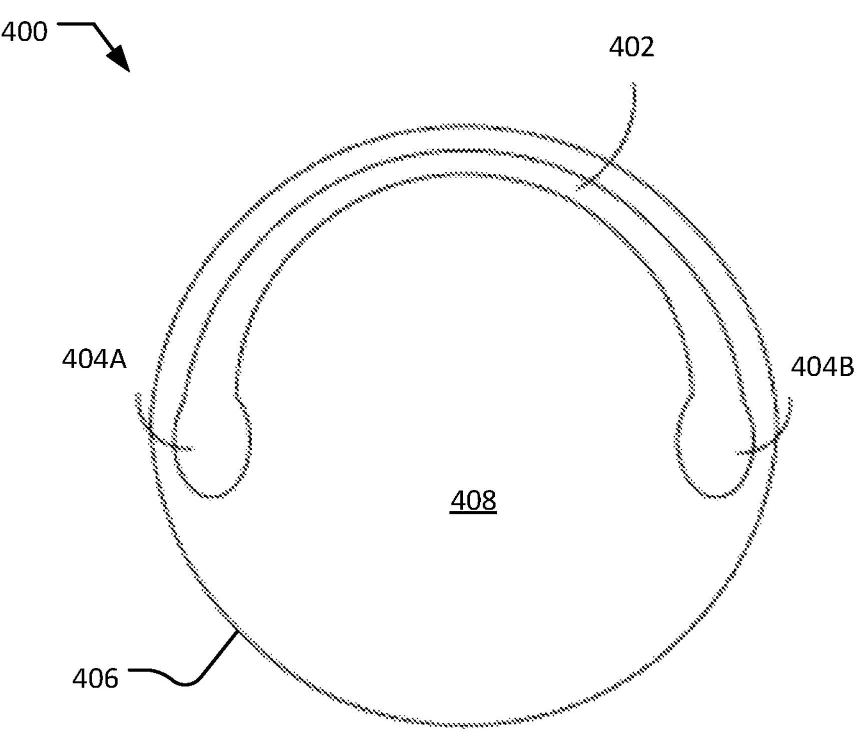
FIG. 4A illustrates a cross section of a stent-graft having flow ends, within an aortic vessel, illustrating an example crescent-shaped minimum cross sectional area with flow ends wider than a central flow portion, according to an aspect of the present disclosure.

FIG. 4A illustrates a cross section of a stent-graft 400 having flow ends, within an aortic vessel 406, illustrating an example crescent-shaped minimum cross sectional area, according to an aspect of the present disclosure. The aortic vessel 406 includes an area 408 in which blood is obstructed from flowing because the stent-graft 400 directs blood to the minimum cross sectional area of its cavity. The example stent-graft 400 is formed such that the example minimum cross sectional area of the cavity includes a left flow end 404A, a central flow portion 402, and a right flow end 404B. As illustrated in the figure, each of the left flow end 404A and the right flow end 404B are wider than the central flow portion 402. The greater width of the left and right flow ends 404A, 404B results in blood flow being directed to the left and right flow ends 404A, 404B due to blood's tendency to flow to the path of least resistance. In some aspects of such an example stent-graft 400, the combined cross sectional area of the left flow end 404A and the right flow end 404B equals between 60-90% of the total minimum cross sectional area. For example, in some instances, at least one of the left flow end 404A or the right flow end 404B has a cross sectional area equal to between 2.1 to 21 $mm^2$.

The wide curvature at the ends of the right and left flow ends 404A, 404B may help increase the fatigue life of the stent-graft 400 as compared to sharp corners at the left and right flow ends 404A, 404B. Fatigue life at the crescent corners of the stent-graft 400 is of particular importance because increasing such fatigue life may help reduce the risk of frame wire fracture. If frame wire fracture occurs, one of the broken ends of the frame wire can puncture the material of the stent frame, thus causing leakage. Additionally or alternatively, one of the broken ends of the frame wire can puncture the wall of a patient's aorta, which could be life-threatening because blood would leak out of the aortic vessel lumen, clinically referred to as aortic dissection.

In various instances, however, an example stent-graft 400 having a minimum cross sectional area illustrated in FIG. 4A may result in more blood flowing through the left flow end

404A as compared to the right flow end 404B, or vice versa. In such an instance, more blood may flow to one of a patient's legs as compared to the other, which is not desired as it could lead to blood circulation complications for the leg receiving less blood.

Figure 4B:
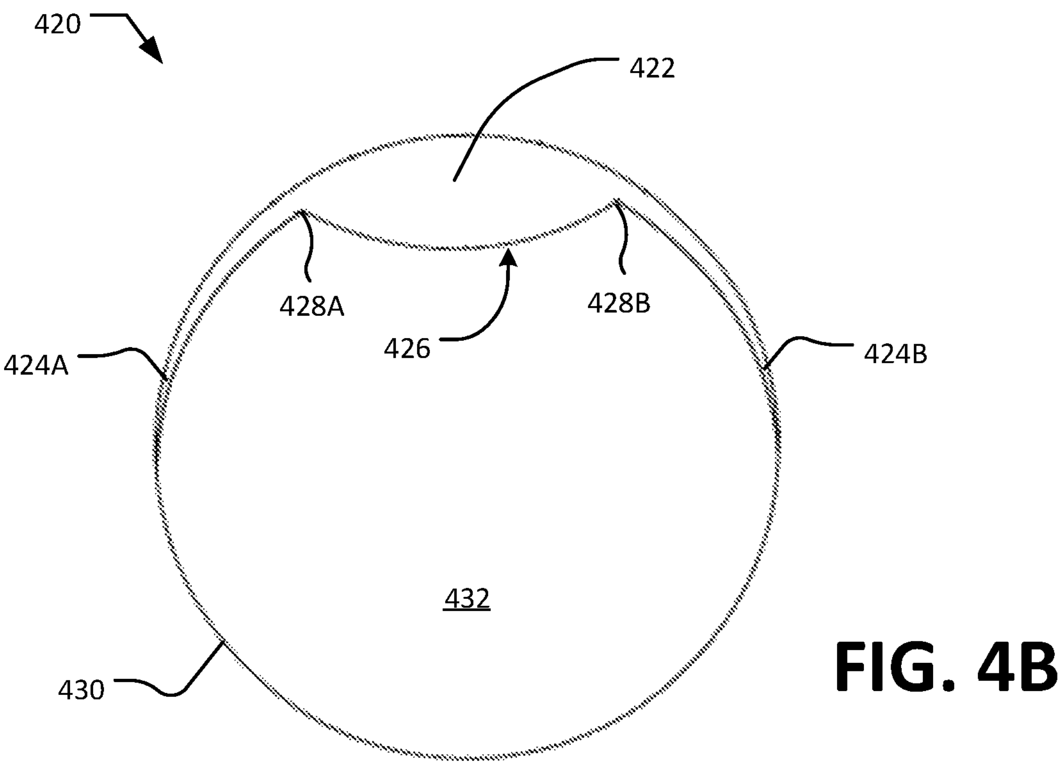
FIG. 4B illustrates a cross section of a stent-graft having flow ends, within an aortic vessel, illustrating an example crescent-shaped minimum cross sectional area with a central flow portion wider than the flow ends, according to an aspect of the present disclosure.

In various aspects, the provided stent-graft may include a central portion that is wider than the left and right flow portions in order to help more evenly distribute blood between each of the patient's legs. FIG. 4B illustrates a cross section of an example stent-graft 420 having flow ends, within an aortic vessel 430, illustrating an example crescent-shaped minimum cross sectional area, according to an aspect of the present disclosure. The aortic vessel 430 includes an area 432 in which blood is obstructed from flowing because the stent-graft 420 directs blood to the minimum cross sectional area of its cavity. The stent-graft 420 is formed such that the example minimum cross sectional area of the cavity includes a left flow end 424A, a central flow portion 422, and a right flow end 424B. As illustrated in the figure, the central flow portion 422 is wider than each of the left flow end 424A and the right flow end 424B. The greater width of the central flow portion 422 results in blood flow being directed to the central flow portion 422 due to blood's tendency to flow to the path of least resistance. Directing blood flow to the central flow portion may help limit the issues described above that may occur with regard to uneven blood distribution to the legs. For instance, by directing the blood to a single central portion, the blood may more evenly distribute between each of the patient's legs. The even blood distribution may also be aided by how the example stent-graft 420 is oriented within a patient, which will be described in more detail below.

In various aspects, the portion of the stent frame forming the central flow portion 422 may include an inner wall 426 that curves away from the outer perimeter of the stent frame that contacts the wall of the aortic vessel 430. The inner wall 426 curving away from the stent frame outer perimeter enables the central flow portion 422 to be wider than the left flow end 424A and the right flow end 424B. In some examples, the inner wall 426 may have a radius of curvature between 0.01 to 3.00 mm. The inner wall 426 may also be formed integrally with, or connected to, each respective inner wall of the portion of the stent frame forming the left flow end 424A and the right flow end 424B, respectively. The stent frame may be folded at each fold axis 428A, 428B where the inner wall 426 meets the inner wall of the left flow end 424A and the right flow end 424B, respectively. The folds enable the central flow portion 422 to expand wider than the left flow end 424A and the right flow end 424B. In some instances, the angle of the respective folds may be between 60 to 270 degrees, such that the greater the angle, the more narrow the central flow portion 422.

In various instances, however, as a patient's blood pressure pulses between systolic and diastolic phases, blood flow may be inconsistent through the minimum cross sectional area of the cavity of the example stent-graft 420. For example, because the cavity may expand in some instances, blood may sometimes flow into the left flow end 424A and/or the right flow end 424B more than intended, or may flow unevenly between the left and right flow ends 424A and 424B as described above. The inconsistent blood flow, in some instances, through the example stent-graft 420 may result in an inconsistent volume of blood being redirected to the kidneys and/or being directed to the patient's legs.

Figure 4C:
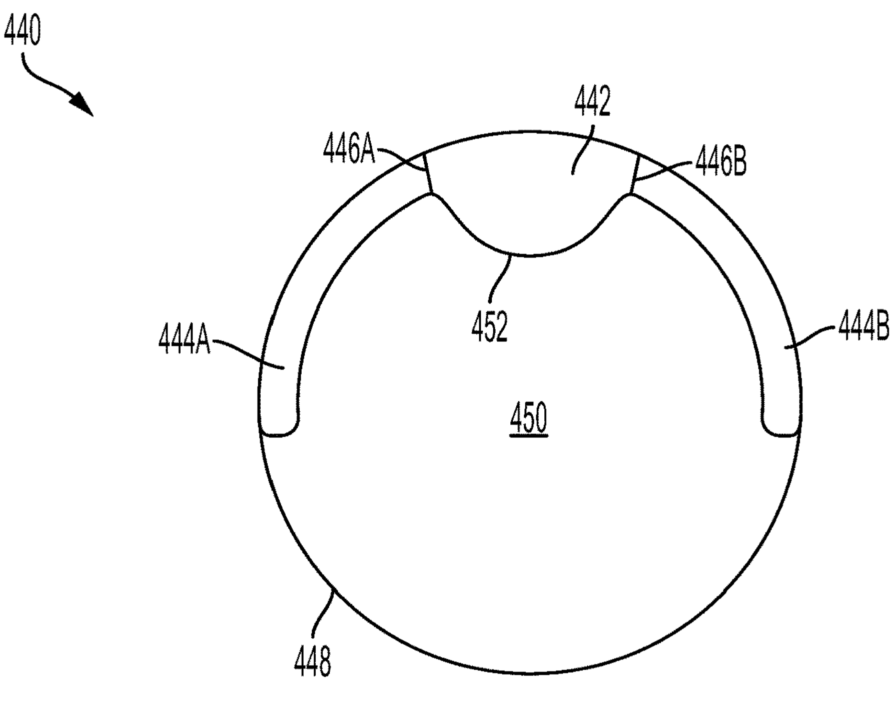
FIG. 4C illustrates a cross section of a stent-graft having flow ends, within an aortic vessel, illustrating an example crescent-shaped minimum cross sectional area with bridges, according to an aspect of the present disclosure.

In various aspects, the provided stent-graft may include bridges connecting the inner wall of the cavity to the outer stent frame perimeter at the minimum cross sectional area. The bridges may help provide blood flow consistency by helping the stent-graft consistently expand evenly at its minimum cross sectional area. FIG. 4C illustrates a cross section of a stent-graft 440 having flow ends, within an aortic vessel 448, illustrating an example crescent-shaped minimum cross sectional area with bridges, according to an aspect of the present disclosure. The aortic vessel 448 includes an area 450 in which blood is obstructed from flowing because the stent-graft 440 directs blood to the minimum cross sectional area of its cavity. The stent-graft 440 is formed such that the example minimum cross sectional area of the cavity includes a left flow end 444A, a central flow portion 442, and a right flow end 444B. Each of the left flow end 444A and the right flow end 444B have softer folds from the outer perimeter stent frame perimeter as compared to the sharp folds of the left flow end 424A and the right flow end 424B of the example stent-graft 420. In other examples, the example stent-graft 440 may include the sharp folds illustrated with regard to the example stent-graft 420, or the example stent-graft 420 may include the softer folds illustrated with regard to the example stent-graft 440.

The example stent-graft 440 additionally includes bridges 446A and 446B. The bridges 446A, 446B connect the outer perimeter of the stent frame, which contacts the wall of the aortic vessel 448, to the inner wall 452 of the stent frame. The inner wall 452 forms the cavity with the stent frame outer perimeter. In some instances, the example stent-graft 440 may include two bridges 446A, 446B, as illustrated. For example, the bridge 446A may connect the inner wall 452 to the stent frame outer perimeter at a fold axis between the left flow end 444A and the central flow portion 442. Similarly, the bridge 446B may connect the inner wall 452 to the stent frame outer perimeter at a fold axis between the right flow end 444B and the central flow portion 442. In other examples, the stent-graft 440 may include a single bridge or more than two bridges. In some aspects, the bridges 446A, 446B only connect the inner wall 452 to the stent frame outer perimeter at the minimum cross sectional area of the cavity. In other aspects, the bridges 446A, 446B may extend a larger portion of the stent (e.g., the entire length of the stent) and may connect the inner wall 452 to the stent frame outer perimeter along the length the bridges 446A, 446B extend.

The inclusion of the bridges 446A, 446B fixing the inner wall 452 to the stent frame outer perimeter may help the cavity of the example stent-graft 440 expand more consistently and uniformly at the minimum cross sectional area. The more consistent and uniform expansion may help limit the inconsistent and/or uneven blood flow issues described above that may occur in connection with the example stent-graft 420. For instance, the bridges 446A, 446B more consistently maintain the cross sectional area of the cavity by preventing one side of the cavity from expanding to a much larger degree than the other side, while still allowing the stent material to flex. In some instances, however, the shear stress placed on the blood flowing through long, thin spaces, such as the left flow end 444A and the right flow end 444B may create an increased risk of hemolysis.

Additionally, because the presently disclosed stent-graft (e.g., the stent graft 440) is reducing the blood volume flowing to the patient's legs, the body may cause the patient's abdominal aorta to dilate in response. Stated differently, the body attempts to correct what it perceives as an unbalanced distribution of blood flow between the upper body over the lower body, caused by the disclosed stent-graft, by dilating the abdominal aorta to attempt to increase the blood flow to the lower body. As the abdominal aorta dilates, the disclosed stent-graft, which exerts radial pressure against the aortic walls, undergoes a conformational change (e.g., expands) so that it maintains contact with the aortic walls. The conformational change may cause the space between the inner and outer walls of the disclosed stent frame cavity to become thinner and thinner as the disclosed stent-graft stretches to conform to the aortic walls. The cavity may become particularly thin at the minimum cross sectional area, and even more particularly thin at the flow ends (e.g., the flow ends 444A and 444B). The increasingly thin cavity at the minimum cross sectional area may further increase the shear stress placed on the blood flowing through presently disclosed stent-graft, and accordingly may further increase the risk of hemolysis.

Figure 4D:
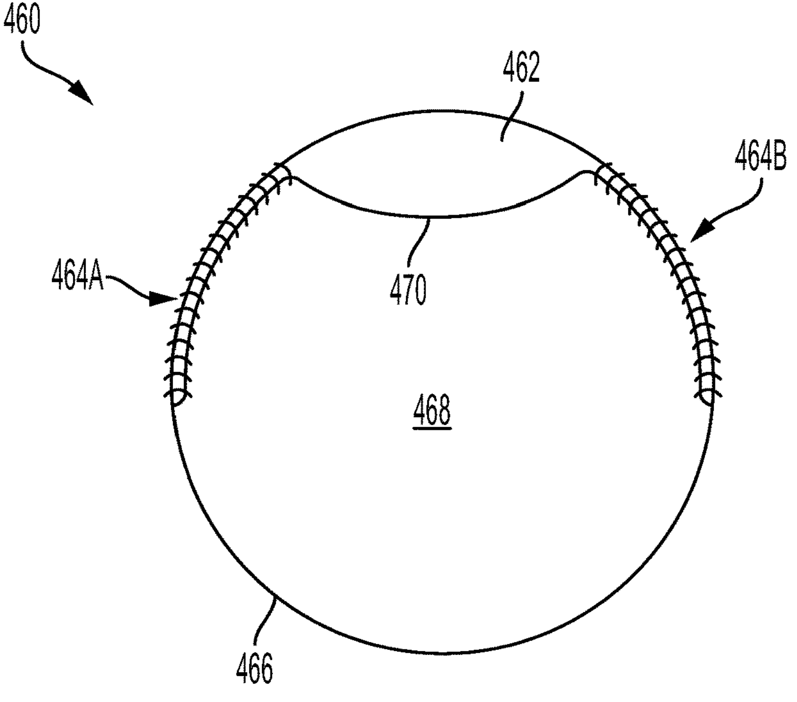
FIG. 4D illustrates a cross section of a stent-graft having flow ends, within an aortic vessel, illustrating an example crescent-shaped minimum cross sectional area with sutured-closed flow ends, according to an aspect of the present disclosure.

In various aspects, the provided stent may include left and right flow ends that are sutured closed to help reduce the risk of hemolysis. FIG. 4D illustrates a cross section of a stent-graft 460 having flow ends, within an aortic vessel 466, illustrating an example crescent-shaped minimum cross sectional area with sutured-closed flow ends, according to an aspect of the present disclosure. The aortic vessel 466 includes an area 468 in which blood is obstructed from flowing because the stent-graft 460 directs blood to the minimum cross sectional area of its cavity. The stent-graft 460 is formed such that the example minimum cross sectional area of the cavity includes a left flow end 464A, a central flow portion 462, and a right flow end 464B. As illustrated, the left flow end 464A is sutured closed such that blood is prevented from flowing through the left flow end 464A. Similarly, the right flow end 464B is sutured closed such that blood is prevented from flowing through the right flow end 464B. For instance, the inner wall 470 of the stent frame may be sutured to the outer perimeter of the stent frame, which contacts the wall of the aortic vessel 466, at each of the left flow end 464A and the right flow end 464B, respectively. In various examples, the sutures used may be formed of a suitable fabric (e.g., polyurethane or polyester).

By suturing the left and right flow ends 464A, 464B closed, preventing blood from flowing through them, blood is directed solely to the central flow portion 462. Thus, blood is prevented from flowing through long, thin spaces that may create an increased risk of hemolysis. Accordingly, the configuration of the example stent-graft 460 may help decrease the risk of hemolysis. Additionally, the sutured-closed left and right flow ends 464A, 464B may help stabilize the central flow portion 462 within a patient's aorta by providing radial force against the aorta walls. The provided radial force may help prevent the stent from being displaced due to forces from the flowing blood. Thus, rather than eliminate the left and right flow ends 464A, 464B entirely, the example stent-graft 460 with sutured-closed left and right flow ends 464A, 464B may be more stabilized within an aorta than stents without left and right flow ends 464A, 464B. Stated differently, including the sutured-closed left and right flow ends 464A, 464B enables the outer perimeter of the example stent-graft 460 at its minimum cross sectional area to contact at least 50% of the aortic wall to provide fixation forces that help prevent undesired axial movement, as described in more detail above.

In some instances, however, the sutured-closed left and right flow ends 464A, 464B may cause blood to pool at the sutured-closed left and right flow ends 464A, 464B. For instance, blood flowing through the cavity to the sutured-closed left and right flow ends 464A, 464B is prevented from continuing, but may also be prevented to a degree from flowing through the central flow portion 462 by the forces exerted by blood flowing through the cavity and straight through the central flow portion 462. Thus, the blood may pool at the sutured-closed left and right flow ends 464A, 464B, which may cause a greater than desired increase in blood pressure upstream the minimum cross sectional area of the cavity. The blood pooling may also cause fatigue of the fabric of the stent-graft 460 that is connected to a stent frame wire at the location of the pooling. For instance, the pooled blood applies stress to the fabric at that location. The fabric fatigue may, in some situations, lead to tears in the fabric and failure of the stent-graft 460.

Figure 5A:
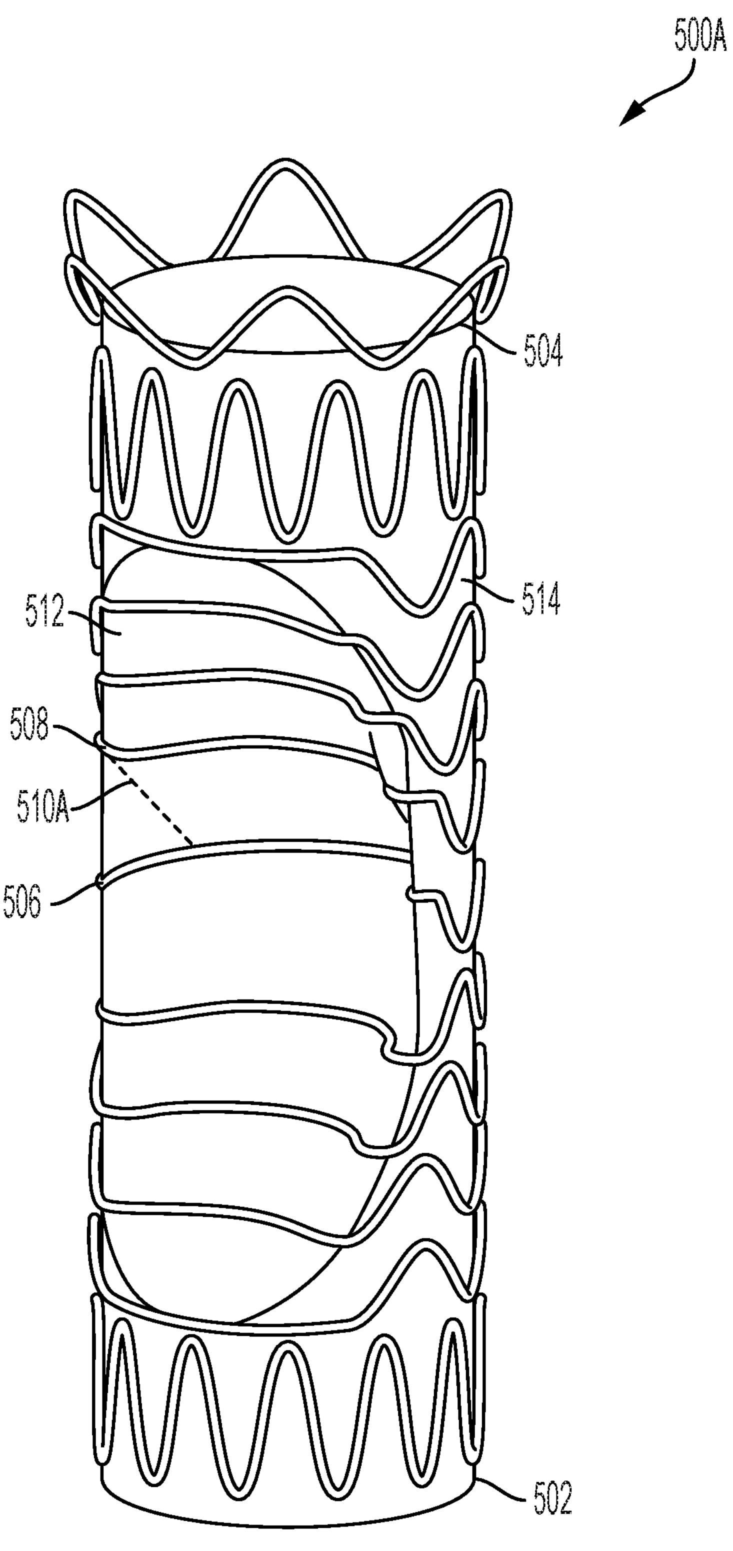
FIG. 5A illustrates an example stent-graft that includes suture lines to funnel blood to a central flow portion, according to an aspect of the present disclosure.

In various aspects, the provided stent-graft may include suture lines upstream the minimum cross sectional area of the cavity to help prevent blood pooling at the sutured-closed left and right flow ends. The suture lines may help gradually direct or funnel blood flowing through the cavity to the central flow portion of the cavity's minimum cross sectional area so that the blood is prevented from reaching the sutured-closed left and right flow ends. FIG. 5A illustrates an example stent-graft 500A that includes a suture line 510A to funnel blood to a central flow portion, according to an aspect of the present disclosure. The example stent-graft 500 includes a proximal end 504 and a distal end 502. The example stent-graft 500 may include a suture line 510A that connects the outer wall 514 of the stent frame material to the inner wall 512 of the stent frame material. It should be appreciated that while only one suture line 510A is illustrated, preventing blood from reaching the left flow end, the example stent-graft 500A may also include a suture line 510A on its other side, preventing blood from reaching the right flow end. The outer wall 514 of material and the inner wall 512 of material may be connected such that fluid is prevented from passing through the suture line 510A. In some examples, the outer wall 514 and the inner wall 512 may be connected by a material that sutures them together. In other examples, the outer wall 514 and the inner wall 512 may be connected along the suture line 510A by other suitable means, such as adhesive material, staples, etc. In other examples still, the outer wall 514 and the inner wall 512 may be integral with one another, rather than connected, at the suture line 510A. For example, the suture line 510A may be a fold between the outer wall 514 and the inner wall 512.

In various aspects, such as the one illustrated in the figure, the suture line 510A may extend between the frame wire 506 at the minimum cross sectional area of the cavity and the next adjacent frame wire 508 upstream the frame wire 506. In other aspects, the suture line 510A may extend a greater portion of the stent frame, for example, to the next frame wire upstream the frame wire 508. The suture line 510A may also extend less than the full distance between adjacent frame wires. The suture line 510A may extend in a straight line from the edge of the stent frame to a point where a flow end meets the central flow portion, such as in the illustrated example. In other examples, the suture line 510A may take other suitable shapes, such as a convex or concave curve.

Figure 5B:
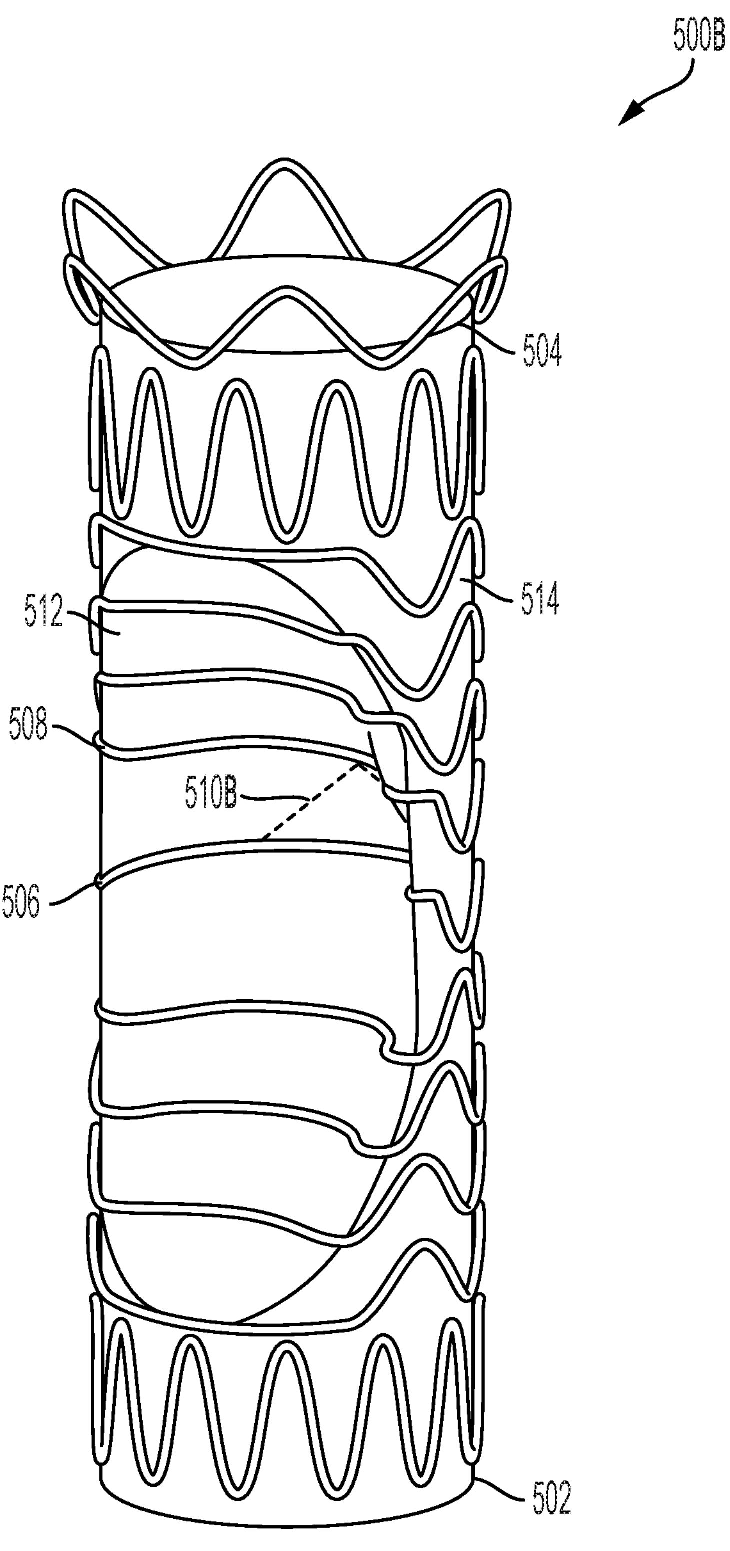
FIG. 5B illustrates an example stent-graft that includes suture lines to funnel blood to flow ends, according to an aspect of the present disclosure.

In other aspects of the present disclosure, the provided stent-graft may include a suture line upstream the minimum cross sectional area of the cavity to help direct blood to a stent-graft's left and right flow ends. For instance, in aspects in which the stent-graft includes a crescent-shaped minimum cross sectional area with flow ends (e.g., FIG. 4A), it may be desirable to direct blood flow to the flow ends, which have a larger cross sectional area than the cavity's central portion. Directing the blood flow in this way may help reduce the shear stress placed on the blood, and thus may help reduce the risk of hemolysis in such stent-graft configurations. FIG. 5B illustrates a stent-graft 500B that includes an example suture line 510B to funnel blood to the flow ends, according to an aspect of the present disclosure. The example suture line 510B is in the shape of an upside down "V" with the point of the "V" at the midline of the stent-graft 500B. In other examples, suture line 510B may take other suitable shapes, such as an upside down "V" with two concave lines, or a single convex line.

The outer wall 514 of material and the inner wall 512 of material may be connected such that fluid is prevented from passing through the suture line 510B. In some examples, the outer wall 514 and the inner wall 512 may be connected by a material that sutures them together. In other examples, the outer wall 514 and the inner wall 512 may be connected along the suture line 510B by other suitable means, such as adhesive material, staples, etc. In other examples still, the outer wall 514 and the inner wall 512 may be integral with one another, rather than connected, at the suture line 510AB. For example, the suture line 510B may be a fold between the outer wall 514 and the inner wall 512. In various aspects, such as the one illustrated in the figure, the suture line 510B may extend between the frame wire 506 at the minimum cross sectional area of the cavity and the next adjacent frame wire 508 upstream the frame wire 506. In other aspects, the suture line 510B may extend a greater portion of the stent frame, for example, to the next frame wire upstream the frame wire 508. The suture line 510B may also extend less than the full distance between adjacent frame wires.

Figure 6:
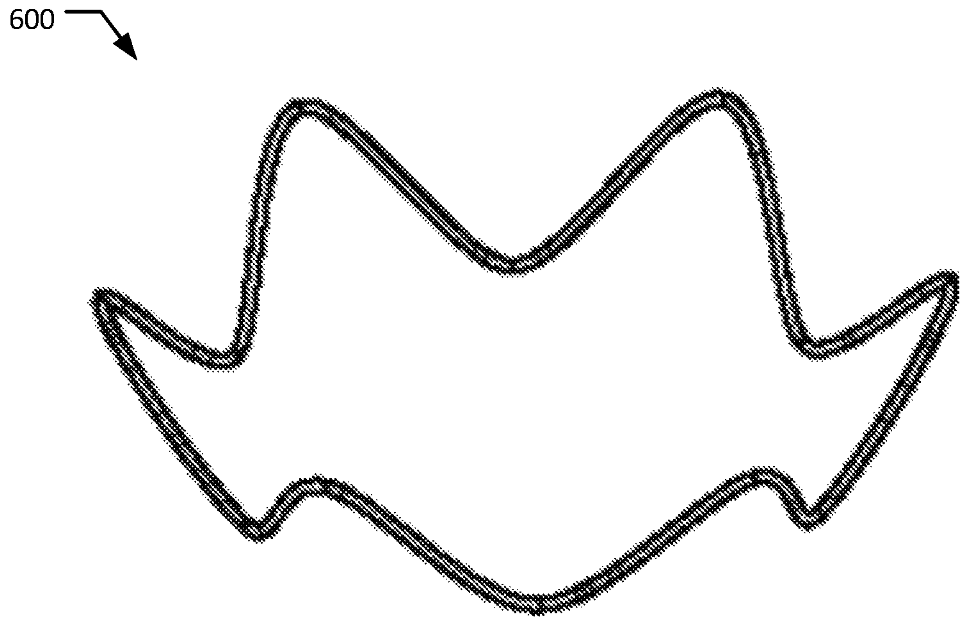
FIG. 6 illustrates an isometric view of an example stent frame wire, according to an aspect of the present disclosure.

As mentioned above, the provided stent-graft may include a plurality of frame wires extending around the stent-graft frame's perimeter. FIG. 6 illustrates a perspective view of an example stent frame wire 600, according to an aspect of the present disclosure. The example stent frame wire 600 is shown having undulating or sinusoidal waves. In various examples, the stent frame wire 600 may be formed to take the shape of any of the described frame wires (e.g., the fixation frame wires 116, 312 the seal frame wires 110A, 110B, 322 or the flow-restricting frame wires 112A, 112B, 114, 310, 314). In some instances, each respective stent frame wire 600 on the provided stent-graft has a diameter between 0.3 to 0.8 mm. The stent frame wire 600 may be composed of a shape-memory material, such as nitinol. The shape memory-material enables the provided stent-graft to expand and return to its resting shape during the blood pressure changes of a patient's heart cycling through systolic and diastolic phases.

In some aspects, each of the respective frame wires on the provided stent-graft includes at least a portion that is undulating. For example, with reference to FIGS. 1A and 1B, the example stent-graft 100 may include seal frame wires 110A and 110B that undulate in the direction of the axis along the length of the example stent-graft 100. The seal frame wires 110A and 110B may undulate along their entire perimeter as they extend around the stent frame 130. The seal frame wires 110A and 110B may help prevent any peritubular leakage from taking place whereby blood may seep between the stent and the patient's aortic wall. For instance, the seal frame wires 110A and 110B may move with the cyclic expansion and contraction of the aorta, which is due to the cyclic blood pressure/flow coming from the heart as it pumps blood. The same description may apply equally to the seal frame wires 322 in reference to FIGS. 3A and 3B.

The example stent-graft 100 may also include flow-restricting frame wires 112A, 112B, and 114 that extend around the stent frame 130 perimeter within the flow restricting portion 118. The flow-restricting frame wires 112A, 112B, and 114 may undulate in the direction of the axis along the length of the example stent-graft 100 while extending around the outer perimeter of the stent frame 130, but may include a curved portion (e.g., the curved portion 136) that curves perpendicularly to that direction while extending along the concave surface 106. For instance, the concave surface 106 extends into the cavity, and thus to extend along the perimeter of the stent frame 130, the curved portion of the flow-restricting frame wires 112A, 112B, and 114 may also extend in that direction. The flow-restricting frame wires 112A, 112B, 114 are accordingly crescent-shaped when viewed down the axis along the length of the example stent-graft 100. For example, the undulating portion and the curved portion form the crescent shape. In some examples, the curved portion of the flow-restricting frame wires 112A, 112B, and 114 that extends along the concave surface 106 may additionally undulate along the perimeter of the stent frame 130. The stent frame wires 112A, 112B, and 114 may provide support to maintain the reduced cross sectional area of the cavity 132 within the flow restricting section 118 of the example stent-graft 100. The undulating portion of each flow-restricting frame wire 112A, 112B, 114 may also cause the provided stent-graft to radially expand against a patient's aortic wall.

In some aspects, the one or more flow-restricting frame wires 112A, 112B, 114 may have a static configuration in which their shapes remain constant in response to changes in blood pressure. In other aspects, one or more flow-restricting frame wires 112A, 112B, 114 may be configured to expand and contract in response to changes in blood pressure. For instance, because the undulating portion of each flow-restricting frame wire 112A, 112B, 114 is fixed against the patient's aortic wall, the curved portion of each flow-restricting frame wire 112A, 112B, 114 may alter its curvature in response to changes in blood pressure, which increases and decreases the cross sectional area of the cavity. For example, a curved portion may become flatter in response to increased blood pressure and may return to its resting curvature in response to decreased blood flow and pressure. When the curved portion becomes flatter, the space between the undulating portion and the curved portion, and thus the cavity, becomes larger. The amount that a curved portion alters its curvature may depend on the diameter of the flow-restricting frame wires. For instance, a thicker frame wire may be stiffer and thus may require a greater blood pressure to cause the frame wire to alter its shape.

In some instances, one or more flow-restricting frame wires 112A, 112B, 114 may be configured such that in its resting state, the undulating portion and the curved portion close the cavity completely. In such instances, blood may not flow through the flow restricting section until blood pressure equal to or greater than a threshold pressure forces the undulating portion and the curved portion of the flow-restricting frame wire 112A, 112B, 114 apart. In some examples, the flow-restricting frame wire 114 at the minimum cross sectional area 120 may be the only flow-restricting frame wire that completely closes the cavity. The above-described configuration of flow-restricting frame wires including shape-altering curved portions has a more valvular nature to it and can be applied to manage patient conditions that are contributed to or caused by chronic hypotension where upper body hypotension is more pronounced and in more urgent need of long-term correction. The above description regarding the flow-restricting frame wires 112A, 112B, 114 may apply equally to the flow-restricting frame wires 310, 314 in reference in FIGS. 3A and 3B.

Figure 7:
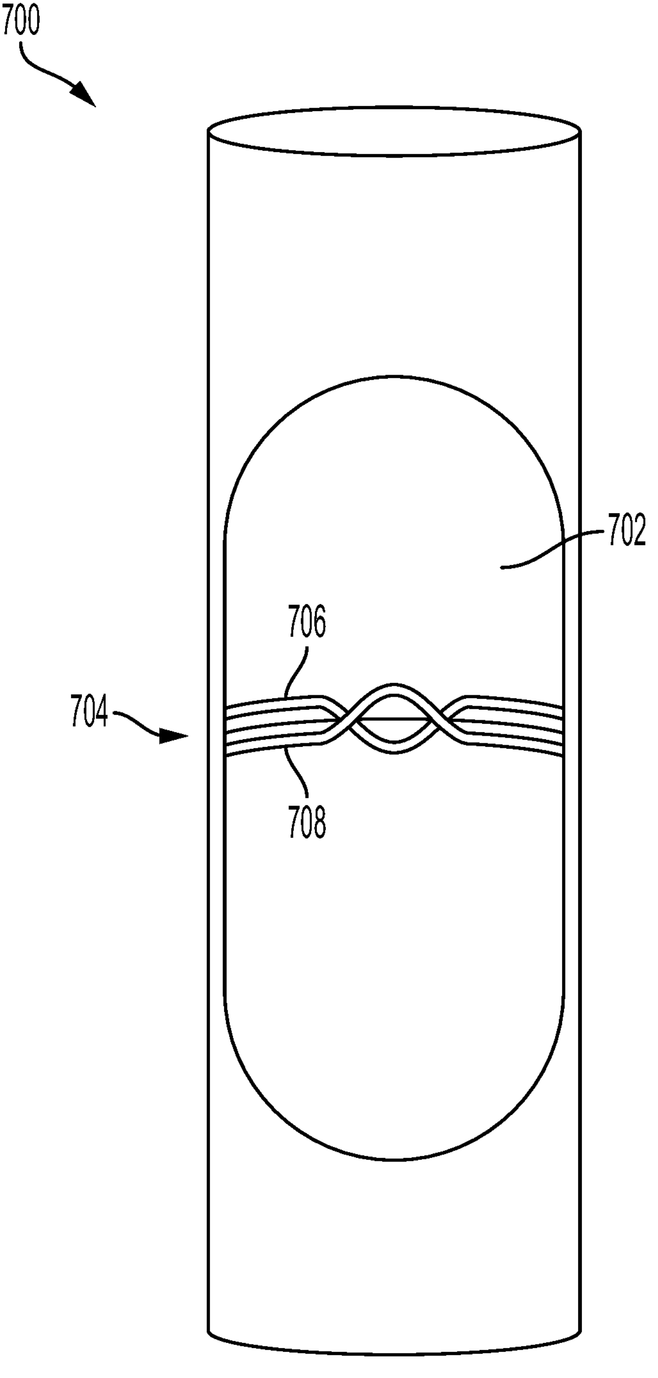
FIG. 7 illustrates a front view of an example stent-graft that includes two stent frame wires around the minimum cross sectional area of the cavity, according to an aspect of the present disclosure.

In some examples, the provided stent-graft, may include more than one flow-restricting frame wire 114 extending around the stent frame perimeter at the minimum cross sectional area of the cavity. FIG. 7 illustrates a front view of an example stent-graft 700 that includes two flow-restricting frame wires around the minimum cross sectional area of the cavity, according to an aspect of the present disclosure. The example stent-graft 700 includes a concave surface 702 forming a flow restricting section and a minimum cross sectional area 704 of the cavity. The example stent-graft 700 may also include an inner stent frame wire 706 and an outer stent frame wire 708 disposed around the inner stent frame wire 706. For instance, the inner stent frame wire 706 and the outer stent frame wire 708 may undulate as illustrated such that they intersect at a number of points. In an example, the inner stent frame wire 706 and the outer stent frame wire 708 may intersect at substantially ninety degree angles. It should be appreciated that FIG. 7 only illustrates the inner stent frame wire 706 and the outer stent frame wire 708 on the example stent-graft 700 for the sake of clarity and that the example stent-graft 700 may include all of the various aspects discussed in the present disclosure.

In other instances, the example stent-graft 700 may include more than two frame wires at the minimum cross sectional area 704 of the cavity, for example, a third frame wire disposed around the outer stent frame wire 708. In some aspects, the stent-graft 700 may have an inner stent frame wire 706 and an outer stent frame wire 708 at more than just the minimum cross section area 704 of the cavity. For example, multiple or all of the flow-restricting frame wires within the flow-restricting section of the concave surface 702 may include an inner stent frame wire 706 and an outer stent frame wire 708. Such flow-restricting frame wires may also include more than two frame wires, such as a third frame wire disposed around the outer stent frame wire 708.

In various aspects, the inner stent frame wire 706 and the outer stent frame wire 708 may both be composed of a shape-memory material, such as nitinol. The shape-memory transition temperature of the outer stent frame wire 708 (e.g., 40° C.) may be greater than the shape-memory transition temperature of the inner stent frame wire 706 (e.g., 35° C.). In some instances, a patient's congestive heart failure may progress resulting in even less blood flow to the patient's kidneys than when the provided stent-graft was first inserted within the patient's aorta. The different shape-memory transition temperatures of the inner and outer stent frame wires 706 and 708 may help constrict the minimum cross sectional area 704 of the cavity even further so as to increase further the blood pressure upstream the minimum cross sectional area 704 and cause additional blood to flow to the renal arteries and the kidneys. In examples in which the stent-graft 700 includes more than two stent frame wires surrounding the minimum cross sectional area 704, the third stent frame wire surrounding the outer stent frame wire 708 may have a transition temperature (e.g., 42° C.) greater than the transition temperature of the outer stent frame wire 708. A fourth stent frame wire surrounding the third stent frame wire may have a transition temperature (e.g., 45° C.) greater than the third stent frame wire, and so forth.

For example, a patient's average body temperature may be 37.5° C., which is above the shape-memory transition temperature of the inner stent frame wire 706 (e.g., 35° C.), but below the shape-memory transition temperature of the outer stent frame wire 708 (e.g., 40° C.). Thus, the shape-memory characteristics of the inner stent frame wire 706 have been activated, but they have not been activated for the outer stent frame wire 708. If a patient's congestive heart failure progress, as described above, heat may be applied to the outer stent frame wire 708 to a temperature at or above 40° C. to activate its shape-memory characteristics. For instance, activating the shape-memory characteristics of the outer stent frame wire 708 may cause the outer stent frame wire 708 to constrict to a desired shape such that it constricts the inner stent frame wire 706 and the stent frame, therefore decreasing the minimum cross sectional area 704 of the cavity. The outer stent frame wire 708 then remains in the desired, constricted shape until a very low temperature (e.g., 15° C.) is reached, which is unlikely to occur. Heat may be applied to the outer stent frame wire 708 by catheter-based heat ablation via an expandable balloon for example or by other suitable methods that allow the example stent-graft 700 to remain within the patient.

Figure 1A:
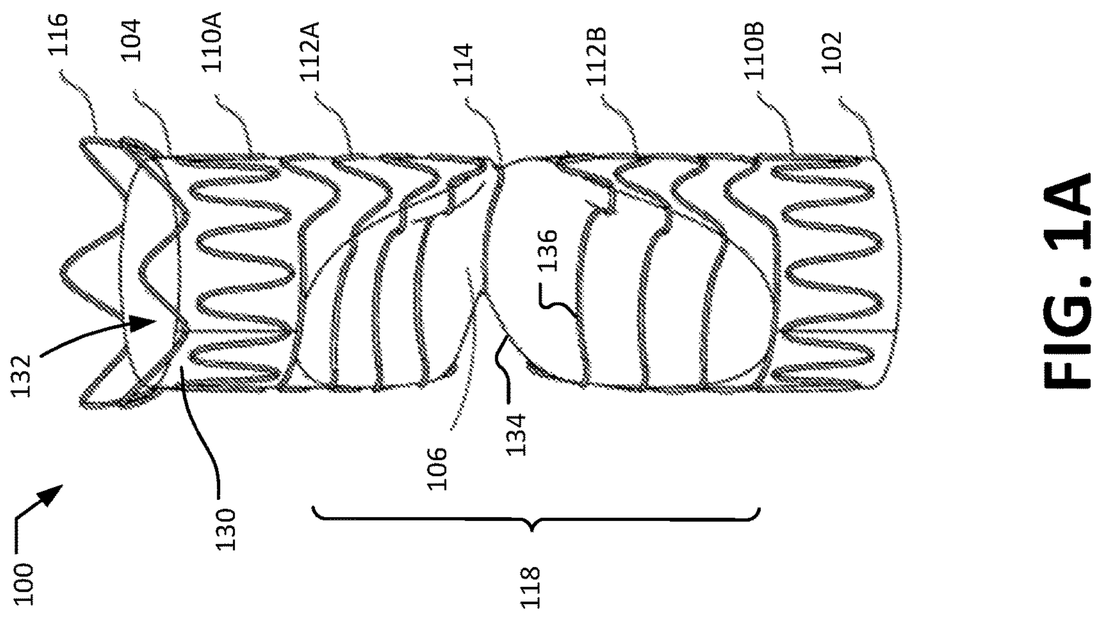

In some aspects of the present disclosure, the provided stent-graft may include a fixation frame wire, such as the fixation frame wire 116 of the example stent-graft 100 (FIG. 1) and the fixation frame wire 312 of the example stent-graft 300 (FIG. 3). Reference will be made to the fixation frame wire 312 and the example stent-graft 300 as illustrated in FIG. 3, though it should be appreciated that the description applies to the fixation frame wire 116 as well. The fixation frame wire 312 may undulate and extend outward beyond the outer perimeter of the stent frame 316. The outward extension of the fixation frame wire 312 may help fix the stent-graft 300 to an aorta wall and prevent it from being displaced by blood displacement forces. In the illustrated example, the stent-graft 300 includes the fixation frame wire 312 at its proximal end 304. In some examples, the stent-graft 300 may additionally or alternatively include a fixation frame wire 312 at its distal end 302.

In some aspects of the present disclosure, the provided stent-graft may include a wireless percutaneous pressure monitor. The wireless percutaneous pressure monitor may help a medical professional gauge how the stent-graft is affecting the patient, for instance, if the stent-graft is generating desired blood pressure upstream the stent-graft and/or is causing a satisfactory blood pressure downstream the stent-graft. The medical professional may use such information to make decisions regarding the patient's treatment plan, such as whether to activate an outer stent frame and further restrict the stent-graft, as described above.

The wireless percutaneous pressure monitor may be wireless. It may also be powered by radiofrequency energy from an external device. The pressure monitor may be integrated with the provided stent-graft near its proximal and/or its distal end. In some instances, the pressure monitor may be integrated with the stent-graft based on fabric or metal suturing, magnets, or a mechanical clip holder. The mechanical clip holder may anchor to a frame wire on the stent-graft on one end of the holder and may attach to the pressure monitor on the other end of the holder.

Figure 8:
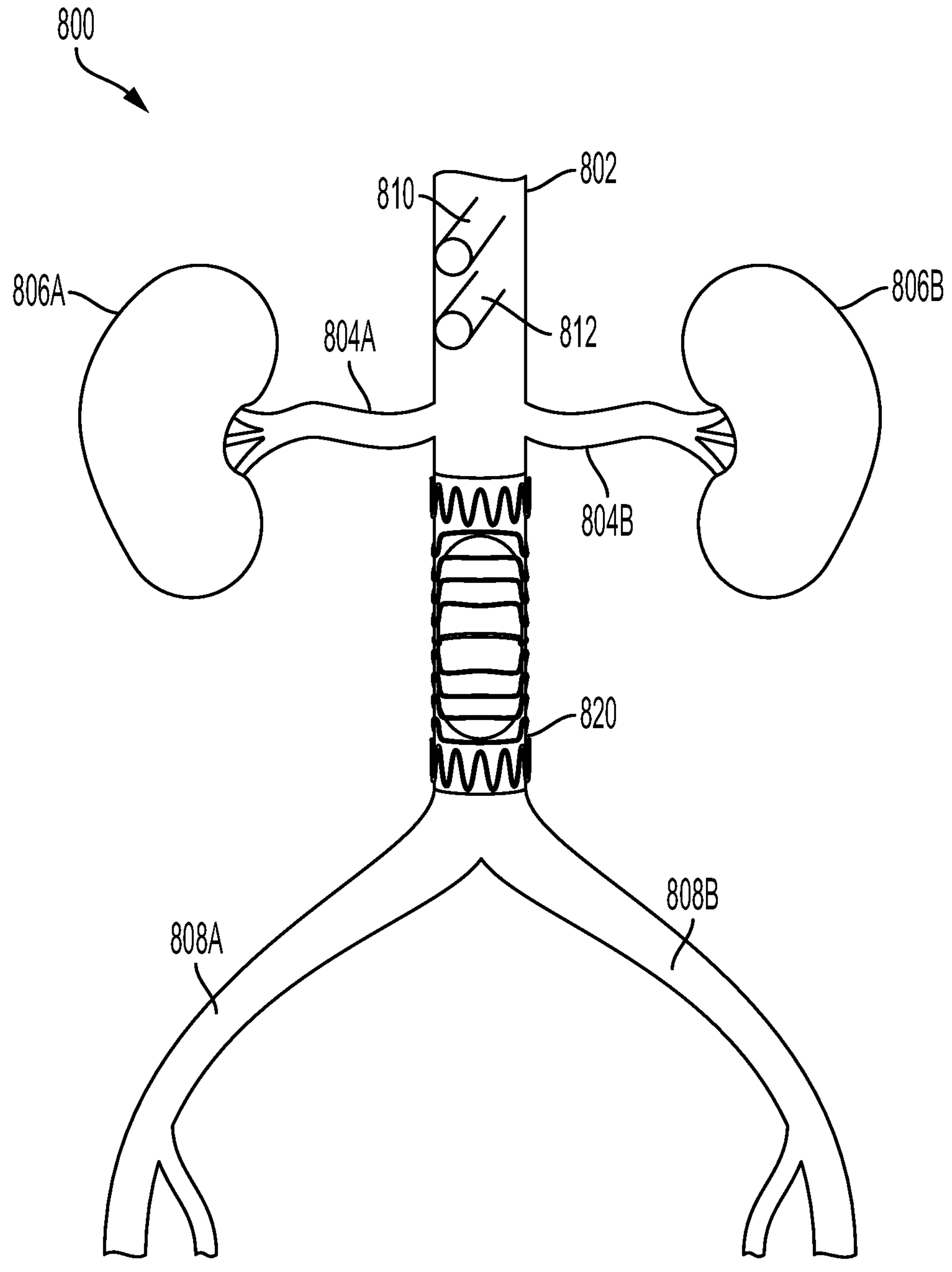
FIG. 8 illustrates a patient with a stent-graft of the present disclosure inserted within the patient's abdominal aorta, according to an aspect of the present disclosure.

FIG. 8 illustrates a patient 800 with a provided stent-graft inserted within the abdominal aorta of the patient 800, according to an aspect of the present disclosure. The example stent-graft 820 is shown inserted within the abdominal aorta 802 below the renal arteries 804A, 804B and above the branching out of the common iliac arteries 808A, 808B. The renal arteries 804A and 804B lead to the kidneys 806A and 806B, respectively. Also shown, are the celiac trunk artery 810 and the superior mesenteric artery 812. The example positioning of the stent-graft 820 enables blood pressure to increase upstream the stent-graft 820. The increased blood pressure may help cause more complete filling of the renal arteries 804A, 804B so that an increased volume of blood is directed to the kidneys 806A, 806B as compared to a patient 800 without the stent-graft 820.

The stent-graft 820 may be oriented within the abdominal aorta 802, as illustrated, with the minimum cross sectional area of the cavity evenly distributed between the left and right sides of the patient 800. For instance, if the minimum cross sectional area of the cavity is oriented towards the left side of the patient 800, blood may be more likely to flow to the common iliac artery 808B of the left side of the patient 800, accordingly resulting in an uneven distribution of blood to the legs. The stent-graft 820 may also be oriented, as illustrated, with the central flow portion of the minimum cross sectional area of the cavity oriented towards the posterior of the abdominal aorta. The posterior orientation may help direct blood flow to the kidneys 806A, 806B. For instance, if the central flow portion is oriented towards the anterior of the abdominal aorta, blood may be more likely to flow to the celiac trunk artery 810 and/or the superior mesenteric artery 812, which are located on the anterior portion of the abdominal aorta. In some examples, the stent-graft 820 may include a radiopaque marker to help assist a medical professional in properly aligning the stent-graft 820 within the abdominal aorta 802 of the patient 800.

Figure 9B:
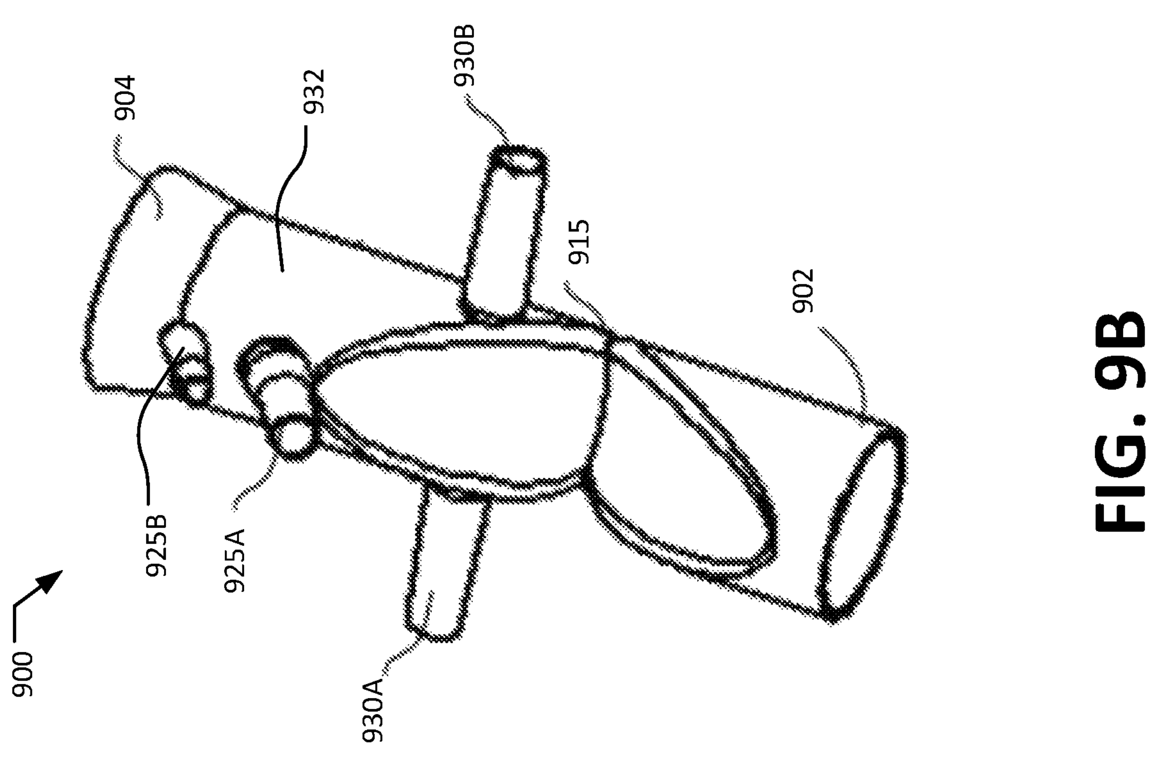
FIGS. 9A and 9B illustrate a front view and isometric view, respectively, of an example stent-graft including graft branches, according to an aspect of the present disclosure.
Figure 9A:
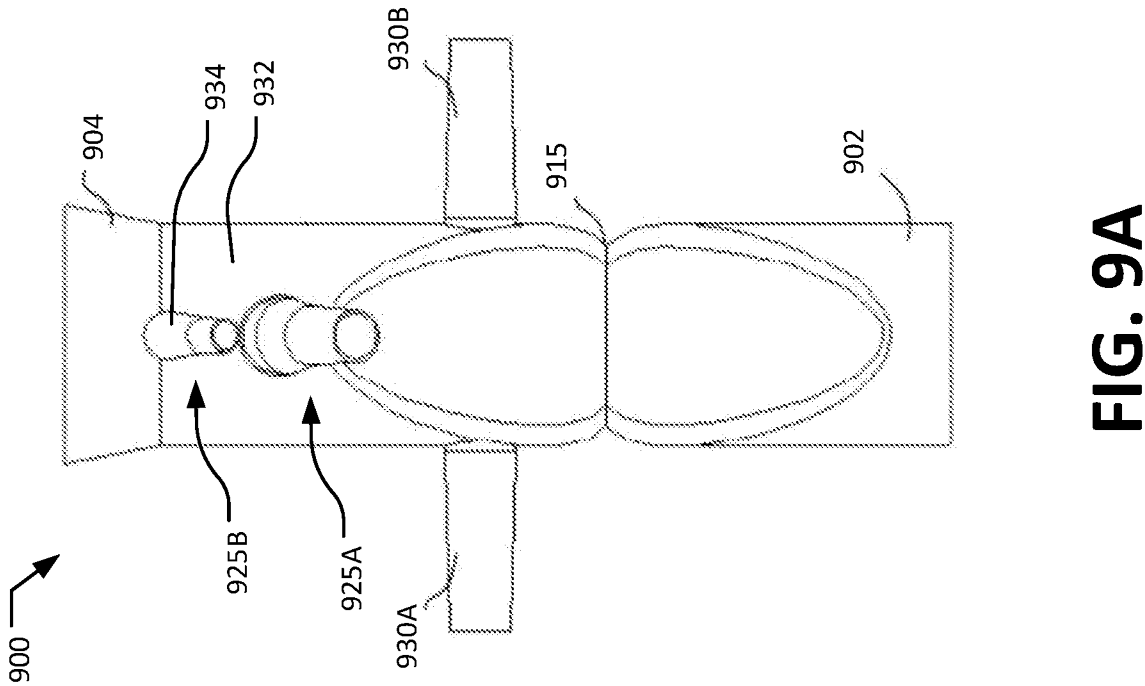

In some instances of the present disclosure, the provided stent-graft may include graft branches for directing blood flow. FIGS. 9A and 9B illustrate a front view and perspective view, respectively, of an example stent including graft branches, according to an aspect of the present disclosure. The example stent-graft 900 includes a stent frame 932 with a proximal end 904 and a distal end 902. The example stent-graft 900 may also include a minimum cross sectional area 915 of a cavity extending through the stent-graft 900. Kidney graft branches 930A and 930B in fluid communication with the cavity may extend from the stent frame 932. In such examples, the stent-graft 900 may be positioned within a patient's abdominal aorta such that each respective kidney graft branch 930A and 930B are positioned within a respective renal artery. The kidney graft branches 930A and 930B may help more definitively direct blood flow to the kidneys because the kidney graft branches 930A and 930B are inserted within the renal arteries. The kidney graft branches 930A and 930B may also help fix the main body of the stent-graft 900 within the abdominal aorta.

The stent-graft 900 may additionally include one or more secondary graft branches that are in fluid communication with the cavity. For instance, the stent-graft 900 may include the secondary graft branch 925A and the secondary graft branch 925B. A secondary graft branch may include a fluid volume reducing portion. The fluid volume reducing portion may create an increased fluid pressure downstream the secondary graft branch so that more blood flows to the kidney graft branches 930A, 930B than if the secondary graft branch did not have the fluid volume reducing portion. For example, the fluid volume reducing portion may be a portion of the secondary graft branch that reduces in cross-sectional area along the secondary graft branch, such as the fluid volume reducing portion 934 of the secondary graft branch 925B.

In such instances in which the stent-graft 900 includes secondary graft branches, the stent-graft 900 may be configured such that when the kidney graft branches 930A and 930B are positioned within respective renal arteries, the secondary graft branch 925A may be positioned within the superior mesenteric artery and the secondary graft branch 925B may be positioned within the celiac trunk artery. In some examples, the stent-graft 900 may include only one of the secondary graft branches 925A, 925B. The secondary graft branches 925A, 925B may help more definitively direct blood flow to the superior mesenteric artery and the celiac trunk artery. The secondary graft branches 925A, 925B may also help fix the stent-graft 900 within the abdominal aorta.

A patient may, in some instances, have an undesired volume of blood flow to the patient's intercostal artery branches in the patient's thoracic aorta. For example, the increased blood pressure created by the provided stent-graft upstream the cavity's minimum cross sectional area may create an undesired volume of blood flow to the patient's intercostal artery branches. In some examples, to help prevent the undesired volume of blood flow to the intercostal artery branches, the provided stent-graft may extend from a patient's thoracic aorta to the patient's abdominal aorta. In such examples, the stent-graft may include a blocking sleeve that prevents blood from flowing into the intercostal artery branches.

Figure 10:
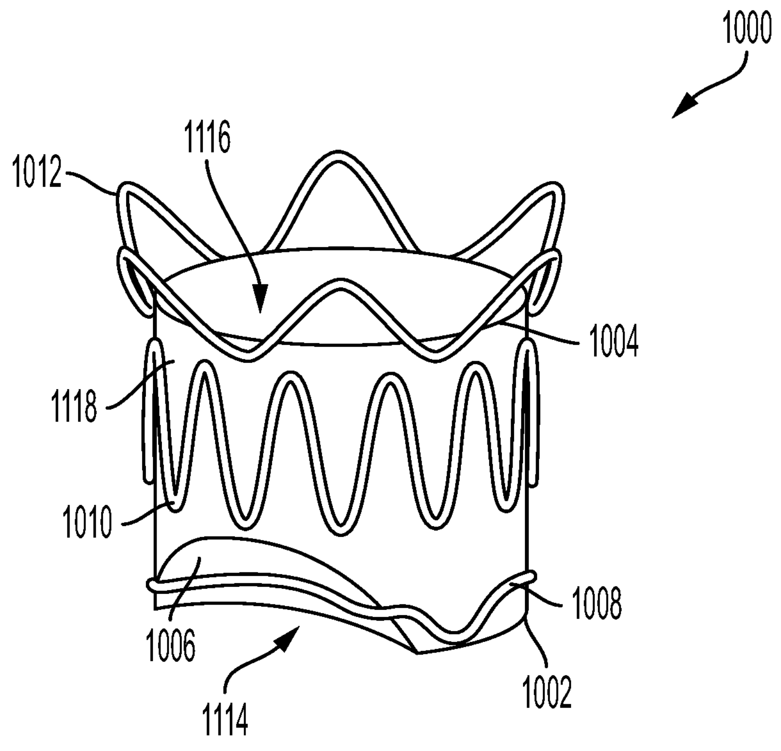
FIG. 10 illustrates an isometric view of an example stent graft for urethral applications, according to an aspect of the present disclosure.

In various aspects of the present disclosure, the provided stent-graft may be adapted to help treat patients with urinary incontinence. FIG. 10 illustrates an isometric view of an example stent-graft 1000 adapted for placement within a patient's urethra, according to an aspect of the present disclosure. The example stent-graft 1000 includes a stent frame 1118 that forms a cavity 1116 extending from an opening at a proximal end 1004 of the stent-graft 1000 to an opening at a distal end 1002 of the stent-graft 1000. Thus, a fluid (e.g., urine) may flow into the proximal opening, through the cavity, and out the distal opening.

The stent-graft 1000 may include a fixation frame wire 1012 that extends around the perimeter of the stent frame 1118 at the proximal opening 1004. The description above with respect to the fixation frame wires 116 and 312 may apply equally to the fixation frame wire 1012, except adapted to fixing the stent-graft 1000 within a patient's urethra. The stent-graft 1000 may also include a seal frame wire 1010 that extends around the perimeter of the stent frame 1118. The description above with respect to the seal frame wires 110A, 110B, and 322 may apply equally to the seal frame wire 1010, except adapted to preventing urine leakage between the stent-graft 1000 and the urethral wall.

The stent-graft 1000 may also include a flow-restricting frame wire 1008 extending around the perimeter of the stent frame 1118 at the distal opening 1002. The flow-restricting frame wire 1008 is configured expand and contract in response to changes in fluid (e.g., urine) pressure, as described above in connection with the flow-restricting frame wires 112A, 112B, 114, 310, and 314. The flow-restricting frame wire 1008 is also configured to close the cavity completely when in a resting state, as described above as well in connection with the flow-restricting frame wires 112A, 112B, 114, 310, and 314. Fluid (e.g., urine) is prevented from flowing through the cavity of the stent graft 1000 until fluid pressure equal to or greater than a threshold pressure (e.g., 20 mmHg) forces apart the undulating portion and the curved portion of the flow-restricting frame wire 1008. The threshold pressure, in various instances, may be between approximately 10-40 mmHg. The flow-restricting frame wire 1008 therefore has a valvular nature to it that can be applied to prevent urine from passing through when a patient does not have to urinate, but allow urine to pass through when a patient's bladder is sufficiently full and the patient does need to urinate.

The threshold pressure needed to open the flow-restricting frame wire 1008 may depend on the diameter of the flow-restricting frame wire 1008. For instance, a thicker frame wire may be stiffer and thus may require a greater fluid pressure to cause the flow-restricting frame wire 1008 to alter its shape. The diameter of the flow-restricting frame wire 1008 may therefore be adapted to be suitable for a particular patient. In various instances, the diameter of the flow-restricting frame wire 1008 may be between 0.05-0.5 millimeters. For example, the flow-restricting frame wire 1008 may have a diameter of 0.1 millimeters.

Additionally, in the above-described configuration, the undulating portion of the flow-restricting frame wire 1008 contacts a patient's urethral wall. The curved portion of the flow-restricting frame wire 1008, however, does not contact the patient's urethral wall. This configuration enables a medical professional to use an instrument (e.g., tweezers) to grab the curved portion of the flow-restricting frame wire 1008 when removing the stent-graft 1000 in situations in which it is desired that the stent-graft 1000 be removed. Enabling the medical professional to grab the curved portion, which does not contact the urethral wall helps prevent incidental damage to the patient's urethral wall from an instrument.

The example stent-graft 1000 may be structured such that a cross sectional area of the cavity 1116 decreases from a cross sectional area at the proximal end 1004 to a minimum cross sectional area 1114 at the distal end 1002. In various examples, the diameter of the stent-graft 1000 at the proximal end 1004 may be between approximately 9.5-17 millimeters. The diameter of the stent-graft 1000 may be approximately 20-30% larger compared to the diameter of a patient's urethra in order to utilize outward radial force to prevent displacement of the stent-graft 1000 within the patient's urethra. The minimum cross sectional area 1114 may be crescent-shaped, such as the crescent-shaped configurations of the minimum cross sectional areas described above. In such aspects, the stent frame 1118 includes a concave surface 1006 extending into the cavity 1116 to decrease the cross sectional area of the cavity 1116. As described above, the flow-restricting frame wire 1008 may close the cavity of the stent-graft 1000 completely in a resting state and thus the minimum cross sectional area of the stent-graft 1000 in a resting state is equal to zero. When a threshold hydrostatic pressure expands the flow-restricting frame wire 1008, the minimum cross sectional area may, in various instances, expand to a cross sectional area equal to approximately 8-530 $mm^2$ to allow urine to pass through and exit the patient's body.

Figure 11:
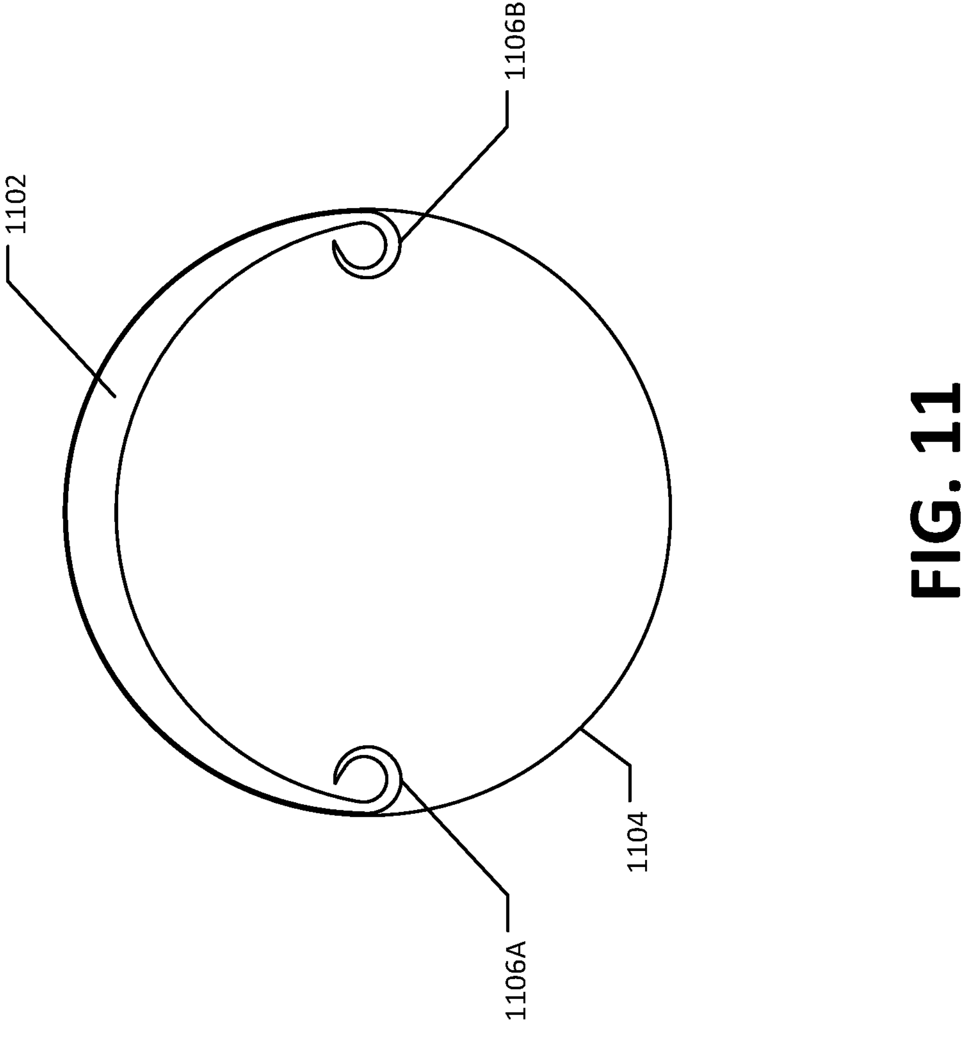
FIG. 11 illustrates an example cross section at the minimum cross sectional area of the example stent-graft in an expanded state within a urethra, according to an aspect of the present disclosure.

Unlike blood, urine does not coagulate, and therefore urine does not share the same shear stress concerns described above with respect to blood. Because urine is not susceptible to shear stress complications, the stent-graft 1000 may, in various instances, be structured with a different minimum cross sectional area than the congestive heart failure adaptations described above. For instance, FIG. 11 illustrates an example cross section 1100 at the minimum cross sectional area 1102 of the example stent-graft 1000 in an expanded state within a urethra 1104, according to an aspect of the present disclosure. Urine may flow through thin spaces without the shear stress concerns and risk of hemolysis associated with blood, and therefore a stent-graft structured with a cavity as illustrated in FIG. 11 does not pose a risk to patients in adaptations of the present disclosure to help treat urinary incontinence.

The example stent-graft 1000 may also be configured such that the cavity at the minimum cross sectional area 1102 includes curled portions 1106A, 1106B. Without the curled portions 1106A, 1106B, a risk of puncturing the wall of the urethra 1104 may be increased due to the sharp edges of the stent-graft 1000. For instance, when urine's fluid pressure is sufficient to expand the stent-graft 1000, the fluid pressure also expands the diameter of the urethra 1104. When the urine's fluid pressure decreases, the diameter of the urethra 1104 decreases and the stent-graft 1000 contracts, which may cause the sharp ends of the stent-graft 1000 to puncture the wall of the urethra 1104. The curled portions 1106A, 1106B help prevent puncturing the wall of the urethra 1104 by preventing the sharp ends of the stent-graft 1000 from contacting the wall of the urethra 1104 as the stent-graft 1000 expands and contracts.

Additionally, because urine does not present shear stress concerns, the example stent-graft 1000 may be configured without the gradual tapering described above with respect to the provided stent-graft's congestive heart failure adaptations. Stated differently, the stent-graft 1000 is constructed without the cross sectional area of the cavity 1116 gradually decreasing to the minimum cross sectional area 1114 and without gradually increasing, or increasing at all, after the minimum cross sectional area 1114. Instead, the stent-graft 1000 may be constructed such that the cross sectional area of the cavity 1116 decreases abruptly from the cross sectional area at the proximal end 1004 to the minimum cross sectional area 1114 at the distal end 1002. This is advantageous because to be inserted within a patient's urethra, the example stent-graft 1000 is smaller than the stent-grafts (e.g., the stent-grafts 100 and 300) adapted for placement in the abdominal aorta to treat congestive heart failure. For example, urinary incontinence is most common in females and the average length of a urethra in a female patient is approximately four centimeters. Female patients have shorter urethral lengths than male patients. Therefore, the abrupt decrease in cross sectional area of the cavity 1116 enables the stent-graft 1000 to be shorter and able to fit within a patient's urethra. In various examples, the stent-graft 1000 may be between five and forty millimeters in length.

An additional advantage of the example stent-graft 1000 may particularly help patients with an overactive bladder, one type of urinary incontinence. Patients have two urinary sphincters, one at the bladder neck and a second further down the urethra. The first urinary sphincter opens to allow urine to pass through after urine builds up a sufficient degree in the bladder. The second urinary sphincter opens when a patient consciously chooses to open it because the patient desires to urinate. Adjacent to the urethral wall in between the two sphincters is a rich nerve plexus that includes the sensory pudendal nerves, which sense that urine is present and send signals to the bladder. Patients with overactive bladders have bladders that overreact to the signals received from the pudendal nerves. This overreaction from the bladder causes the patients to feel like they have to urinate more often than they should and may cause a patient to involuntarily leak urine when the patient does not desire to urinate.

To help treat patients with an overactive bladder, the example stent-graft 1000 may be configured with a length that extends the length of a patient's urethra between the two sphincters. In such instances, the example stent-graft 1000 prevents urine from direct exposure to the urethral wall between the two sphincters and thus moderates stimulation of the pudendal nerves by allowing passage of urine through the stent-graft 1000 during micturition. By subsiding stimulation of the pudendal nerves, the stent-graft 1000 helps prevent overstimulation of a patient's bladder.

In some instances, the distance between a patient's two urinary sphincters may not be large enough to accommodate the stent-graft 1000. In such instances, the stent-graft 1000 may be configured such that the stent frame 1118 extends an additional distance between the seal frame wire 1010 and the flow-restricting frame wire 1008. For example, when the stent-graft 1000 is positioned within a patient's urethra, such additional distance enables the fixation frame wire 1012 and the seal frame wire 1010 to reside within the urethra between the two urinary sphincters and the flow-restricting frame wire 1008 to reside on the other side of the second urinary sphincter, further down the patient's urethra.

This configuration avoids having the flow-restricting frame wire 1008 interface with the second urinary sphincter's residual function if it were to be positioned within the urinary sphincter. If the flow-restricting frame wire 1008 were positioned within the urinary sphincter, the sphincter's residual contractions may cause the flow-restricting frame 1008, and thus the stent-graft 1000, to shift out of position. The additional distance in the stent frame 1118 between the seal frame wire 1010 and the flow-restricting frame wire 1008 therefore helps prevent interference between the flow-restricting frame wire 1008 and the second urinary sphincter by positioning the flow-restricting frame 1008 further down the patient's urethra than the second urinary sphincter.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated. The scope of the invention is therefore defined by the following claims.

The invention is claimed as follows:

1. A stent-graft comprising:

a stent frame forming a cavity, the cavity extending from a proximal opening of the stent frame to a distal opening of the stent frame, wherein the proximal opening comprises a first aperture, wherein the distal opening comprises a second aperture, wherein the cavity defines a volume that extends from the proximal opening to the distal opening, wherein the stent frame is adapted for a fluid to flow through the cavity from the proximal opening to the distal opening such that an entirety of the fluid that enters from the proximal opening leaves through the distal opening; and a plurality of frame wires extending around a perimeter of the stent frame, wherein the stent frame is formed such that a cross sectional area of the cavity decreases along a first length of a flow restricting section to a crescent-shaped minimum cross sectional area of the cavity and increases along a second length of the flow restricting section, wherein the first length extends from a proximal cross sectional area of the cavity to the crescent-shaped minimum cross sectional area of the cavity and the second length extends from the crescent-shaped minimum cross sectional area of the cavity to a distal cross sectional area of the cavity, wherein the plurality of frame wires includes a single frame wire that conforms to the perimeter of the stent frame at the crescent-shaped minimum cross sectional area, wherein the single frame wire is configured to: (1) maintain the crescent-shaped minimum cross sectional area of the cavity of the stent frame when fluid below a threshold pressure flows through the cavity, and (2) deform when fluid meeting the threshold pressure flows through the cavity, thereby enabling the stent frame to expand at the crescent-shaped minimum cross sectional area.

2. The stent-graft according to claim 1, wherein a perimeter of the stent frame along the flow restricting section includes a concave surface extending into the cavity.

3. The stent-graft according to claim 2, wherein one or more of the plurality of frame wires includes a curved portion extending along the concave surface.

4. The stent-graft according to claim 2, wherein the concave surface of the stent frame perimeter includes a first piece of fabric and the remaining perimeter includes a second piece of fabric, wherein the first piece is connected to the second piece.

5. The stent-graft according to claim 1, wherein the stent-graft is configured such that the stent frame and the plurality of frame wires expand and contract to increase and decrease the cross sectional area of the cavity.

6. The stent-graft according to claim 1, wherein the stent frame is configured such that the minimum cross sectional area of the cavity is equal to between 2% to 20% of the proximal cross sectional area of the stent frame.

7. The stent-graft according to claim 1, wherein the stent frame is configured such that the minimum cross sectional area of the cavity includes a left flow end, a central flow portion, and a right flow end, the left flow end and the right flow end each respectively having a width greater than the central flow portion.

8. The stent-graft according to claim 7, wherein the stent frame includes an outer wall and an inner wall and the outer wall is connected to the inner wall along a line such that fluid flowing from the proximal opening through the cavity is directed to the left flow end and the right flow end and prevented from reaching the central flow portion.

9. The stent-graft according to claim 1, wherein the stent frame is configured such that the minimum cross sectional area of the cavity includes a left flow end, a central flow portion, and a right flow end, the left flow end and the right flow end each respectively having a width less than the central flow portion.

10. The stent-graft according to claim 9, wherein the stent frame at the minimum cross sectional area of the cavity includes an outer wall and an inner wall, and wherein the stent frame is configured such that the inner wall of the central flow portion curves away from the outer wall of the central flow portion.

11. The stent-graft according to claim 9, wherein the stent frame at the minimum cross sectional area of the cavity includes an outer wall and an inner wall, and wherein a first bridge connects the outer wall to the inner wall where the left flow end meets the central flow portion and a second bridge connects the outer wall to the inner wall where the right flow end meets the central flow portion.

12. The stent-graft according to claim 9, wherein the stent frame at the minimum cross sectional area of the cavity includes an outer wall and an inner wall, wherein the outer wall and the inner wall at the left flow end, and the outer wall and the inner wall at the right flow end, are respectively connected together such that fluid is prevented from flowing through the left flow end and the right flow end.

13. The stent-graft according to claim 9, wherein the stent frame includes an outer wall and an inner wall and the outer wall is connected to the inner wall along a line such that fluid flowing from the proximal opening through the cavity is directed to the central flow portion and prevented from reaching the left flow end and the right flow end.

14. The stent-graft according to claim 1, wherein each respective frame wire of the plurality of frame wires includes an undulating portion.

15. The stent-graft according to claim 1, wherein the plurality of frame wires includes a plurality of flow-restricting frame wires within the flow restricting section of the stent frame, and wherein the plurality of flow-restricting frame wires includes the single frame wire that conforms to the perimeter of the stent frame at the crescent-shaped minimum cross sectional area.

16. The stent-graft according to claim 15, wherein each respective flow-restricting frame wire includes an undulating portion and a curved portion.

17. The stent-graft according to claim 16, wherein a radius of curvature between the undulating portion and the curved portion of each respective flow-restricting frame wire is between 0.1 to 1.0 millimeters.

18. The stent-graft according to claim 15, wherein at least one of the plurality of flow-restricting frame wires is configured to contact, when disposed within an abdominal aorta, at least 40% of the perimeter of the abdominal aorta, at least some of the time.

19. The stent-graft according to claim 15, wherein the plurality of flow-restricting frame wires have equal perimeter lengths.

20. The stent-graft according to claim 15, wherein each respective flow-restricting frame wire is constructed from a shape-memory material.

21. The stent-graft according to claim 20, wherein the shape-memory material is nitinol.

22. The stent-graft according to claim 15, wherein the plurality of flow-restricting frame wires includes a first flow-restricting frame wire extending around the perimeter of the stent frame at the minimum cross sectional area of the cavity and a second flow-restricting frame wire disposed around the first flow-restricting frame wire, and wherein the second flow-restricting frame wire has a shape memory transition temperature greater than the first flow-restricting frame wire.

23. The stent-graft according to claim 15, wherein the plurality of frame wires further includes a plurality of second flow-restricting frame wires, each second flow-restricting frame wire disposed around a first flow-restricting frame wire, and wherein each second flow-restricting frame wire has a shape memory transition temperature greater than each first flow-restricting frame wire.

24. The stent-graft according to claim 1, wherein the plurality of frame wires includes a fixation frame wire at the proximal opening of the stent, the fixation frame wire configured to fix the stent to an artery wall.

25. The stent-graft according to claim 1, wherein the stent frame is constructed of one or more fabrics selected from the group consisting of polyurethane, polyester, and polytetrafluoroethylene.

26. The stent-graft according to claim 1, further comprising a wireless percutaneous pressure monitor near at least one of the proximal opening or the distal opening.

27. The stent-graft according to claim 26, wherein the wireless percutaneous pressure monitor is integrated with the stent-graft based on at least one of suturing, magnets, or a mechanical clip.

28. The stent-graft according to claim 1, further comprising two kidney graft branches in fluid communication with the cavity.

29. The stent-graft according to claim 28, further comprising at least one secondary graft branch in fluid communication with the cavity, wherein the at least one secondary graft branch includes a fluid volume reducing portion that reduces the cross-sectional area of the at least one secondary graft branch.

30. The stent-graft according to claim 29, wherein the stent-graft is configured such that each respective kidney graft branch may be inserted within a respective renal artery while the at least one secondary graft branch is inserted within a superior mesenteric artery or a coeliac trunk artery.

31. The stent-graft according to claim 29, wherein the stent-graft is configured such that the proximal opening resides in the thoracic aorta while each respective kidney graft branch of the two kidney graft branches is inserted within a respective renal artery, and wherein the stent-graft further includes a blocking sleeve configured to block fluid flow from the intercostal artery branches when the stent-graft is disposed within an aorta of a patient.

32. The stent-graft according to claim 1, wherein the stent frame is formed with more than one flow restricting section.

33. A stent-graft comprising:

a stent frame forming a cavity, the cavity extending from a proximal opening of the stent frame to a distal opening of the stent frame, wherein the proximal opening comprises a first aperture, wherein the distal opening comprises a second aperture, wherein the cavity defines a volume that extends from the proximal opening to the distal opening, wherein the stent frame is adapted for a fluid to flow through the cavity from the proximal opening to the distal opening such that an entirety of the fluid that enters from the proximal opening leaves through the distal opening;

a fixation frame wire extending around a perimeter of the stent frame at the proximal opening;

a seal frame wire extending around the perimeter of the stent frame; and a flow-restricting frame wire extending around the perimeter of the stent frame at the distal opening, wherein the stent frame is formed such that a cross sectional area of the cavity decreases from the proximal opening to a crescent-shaped minimum cross sectional area of the cavity at the distal opening, and wherein the flow-restricting frame wire is configured to prevent any fluid from flowing through the distal opening that is below a threshold fluid pressure.

34. The stent-graft of claim 33, wherein the stent frame is formed such that the crescent-shaped minimum cross sectional area includes curled portions.

35. The stent-graft of claim 33, wherein the stent frame has a length such that when placed within a patient's urethra, the proximal opening and the distal opening are between a bladder neck sphincter and a secondary sphincter.

36. The stent-graft of claim 33, wherein the stent frame has a length such that when placed within a patient's urethra, the fixation frame wire and the seal frame wire are between a bladder neck sphincter and a secondary sphincter, and the flow-restricting frame wire is between the secondary sphincter and a urethral opening.

37. The stent-graft according to claim 33, wherein the flow-restricting frame wire is constructed from a shape-memory material comprising nitinol.

* * * * *